(12) United States Patent
Dube et al.

(10) Patent No.: US 8,076,359 B2
(45) Date of Patent: Dec. 13, 2011

(54) RENIN INHIBITORS

(75) Inventors: Daniel Dube, St-Lazare (CA); Michel Gallant, Laval (CA); Erich L. Grimm, Baie d'Urfe (CA); Helene Juteau, Quebec (CA); Sebastien Laliberte, Vaudreuil-Dorion (CA); Tom Yao-Hsiang Wu, Hacienda Heights, CA (US)

(73) Assignee: Merck Canada Inc., Kirkland, Quebec (CA)

( * ) Notice: Subject to any disclaimer, the term of this patent is extended or adjusted under 35 U.S.C. 154(b) by 257 days.

(21) Appl. No.: 12/312,454

(22) PCT Filed: Nov. 14, 2007

(86) PCT No.: PCT/CA2007/002044
§ 371 (c)(1),
(2), (4) Date: May 11, 2009

(87) PCT Pub. No.: WO2008/058387
PCT Pub. Date: May 22, 2008

(65) Prior Publication Data
US 2010/0063091 A1    Mar. 11, 2010

Related U.S. Application Data

(60) Provisional application No. 60/859,914, filed on Nov. 17, 2006.

(51) Int. Cl.
*A61K 31/4545*    (2006.01)
*A61K 31/451*    (2006.01)
*C07D 211/60*    (2006.01)

(52) U.S. Cl. ......... 514/318; 514/330; 546/194; 546/225

(58) Field of Classification Search .................. 514/318, 514/330; 546/194, 225
See application file for complete search history.

(56) References Cited

U.S. PATENT DOCUMENTS
6,051,712 A    4/2000    Binggeli et al.

FOREIGN PATENT DOCUMENTS

| CA | 1992/03429 | 3/1992 |
|---|---|---|
| CA | 2004/089903 | 10/2004 |
| WO | WO2006/094763 | 9/2006 |
| WO | WO2008/141462 | 11/2008 |

OTHER PUBLICATIONS

Wayne L. Cody et al. The Discovery and Preparation of Disubstituted Novel Amino-Aryl-Piperridine-Based Renin Inhibitors; Bioorganic & Medicinal Chemistry, Elsevier Science Ltd. GB; vol. 13, No. 1, Jan. 3, 2005; pp. 59-68; *the whole document* also available on—www.sciencedirect.com.

International Search Report; Performed by—Canadian Intellectual Property Office; Date completed—Jan. 24, 2008; By Authorized Officer—Tung Siu (819) 934-6735.

*Primary Examiner* — Kamal Saeed
*Assistant Examiner* — Kristin Bianchi
(74) *Attorney, Agent, or Firm* — Anna Cocuzzo; James L. McGinnis; Mark R. Daniel

(57) ABSTRACT

The present invention relates to disubstituted piperidinyl renin inhibitor compounds having the structure (Formula I) and their use in treating cardiovascular events and renal insufficiency.

9 Claims, No Drawings

RENIN INHIBITORS

CROSS REFERENCE TO RELATED APPLICATION

This application is a U.S. National Phase application under 35 U.S.C. §371 of PCT Application No. PCT/CA2007/002044, filed Nov. 14, 2007, which claims priority under 35 U.S.C. §119(e) from U.S. Provisional Application Ser. No. 60/859,914 filed Nov. 17, 2006.

JOINT RESEARCH AGREEMENT

The claimed invention was made as a result of activities undertaken within the scope of a joint research agreement between Merck & Co., Inc. and Actelion Pharmaceuticals Ltd. The agreement was executed on Dec. 4, 2003. The field of the invention is described below.

FIELD OF THE INVENTION

The invention relates to novel renin inhibitors of the general formula (I). The invention also concerns related aspects including processes for the preparation of the compounds, pharmaceutical compositions containing one or more compounds of formula (I) and especially their use as renin inhibitors in cardiovascular events and renal insufficiency.

BACKGROUND OF THE INVENTION

In the renin-angiotensin system (RAS) the biologically active angiotensin II (Ang II) is generated by a two-step mechanism. The highly specific enzyme renin cleaves angiotensinogen to angiotensin I (Ang I), which is then further processed to Ang II by the less specific angiotensin-converting enzyme (ACE). Ang II is known to work on at least two receptor subtypes called $AT_1$ and $AT_2$. Whereas $AT_1$ seems to transmit most of the known functions of Ang II, the role of $AT_2$ is still unknown.

Modulation of the RAS represents a major advance in the treatment of cardiovascular diseases. ACE inhibitors and $AT_1$ blockers have been accepted to treat hypertension (Waeber B. et al., "The renin-angiotensin system: role in experimental and human hypertension", in Birkenhager W. H., Reid J. L. (eds): *Hypertension*, Amsterdam, Elsevier Science Publishing Co, 1986, 489-519; Weber M. A., *Am. J. Hypertens.*, 1992, 5, 247S). In addition, ACE inhibitors are used for renal protection (Rosenberg M. E. et al., *Kidney International*, 1994, 45, 403; Breyer J. A. et al., *Kidney International*, 1994, 45, S156), in the prevention of congestive heart failure (Vaughan D. E. et al., *Cardiovasc. Res.*, 1994, 28, 159; Fouad-Tarazi F. et al., *Am. J. Med.*, 1988, 84 (Suppl. 3A), 83) and myocardial infarction (Pfeffer M. A. et al., *N. Engl. J. Med.*, 1992, 327, 669).

The rationale to develop renin inhibitors is the specificity of renin (Kleinert H. D., *Cardiovasc. Drugs*, 1995, 9, 645). The only substrate known for renin is angiotensinogen, which can only be processed (under physiological conditions) by renin. In contrast, ACE can also cleave bradykinin besides Ang I and can be by-passed by chymase, a serine protease (Husain A., *J. Hypertens.*, 1993, 11, 1155). In patients inhibition of ACE thus leads to bradykinin accumulation causing cough (5-20%) and potentially life-threatening angioneurotic edema (0.1-0.2%) (Israili Z. H. et al., *Annals of Internal Medicine*, 1992, 117, 234). Chymase is not inhibited by ACE inhibitors. Therefore, the formation of Ang II is still possible in patients treated with ACE inhibitors. Blockade of the $AT_1$ receptor (e.g. by losartan) on the other hand overexposes other AT-receptor subtypes (e.g. $AT_2$) to Ang II, whose concentration is significantly increased by the blockade of $AT_1$ receptors. In summary, renin inhibitors are expected to demonstrate a different pharmaceutical profile than ACE inhibitors and $AT_1$ blockers with regard to efficacy in blocking the RAS and in safety aspects.

Only limited clinical experience (Azizi M. et al., *J. Hypertens.*, 1994, 12, 419; Neutel J. M. et al., *Am. Heart*, 1991, 122, 1094) has been created with renin inhibitors because of their insufficient oral activity due to their peptidomimetic character (Kleinert H. D., *Cardiovasc. Drugs*, 1995, 9, 645). The clinical development of several compounds has been stopped because of this problem together with the high cost of goods. Only one compound containing four chiral centers has entered clinical trials (Rahuel J. et al., *Chem. Biol.*, 2000, 7, 493; Mealy N. E., *Drugs of the Future*, 2001, 26, 1139). Thus, renin inhibitors with good oral bioavailability and long duration of action are required. Recently, the first non-peptide renin inhibitors were described which show high in vitro activity (Oefner C. et al., *Chem. Biol.*, 1999, 6, 127; Patent Application WO97/09311; Märki H. P. et al., *Il Farmaco*, 2001, 56, 21). However, the development status of these compounds is not known.

The present invention relates to the identification of renin inhibitors of a non-peptidic nature and of low molecular weight. Described are orally active renin inhibitors of long duration of action which are active in indications beyond blood pressure regulation where the tissular renin-chymase system may be activated leading to pathophysiologically altered local functions such as renal, cardiac and vascular remodeling, atherosclerosis, and possibly restenosis. So, the present invention describes these non-peptidic renin inhibitors.

The compounds described in this invention represent a novel structural class of renin inhibitors.

SUMMARY OF THE INVENTION

The present invention is directed to certain compounds and their use in the inhibition of the renin enzyme, including treatment of conditions known to be associated with the renin system. The invention includes compounds of Formula I

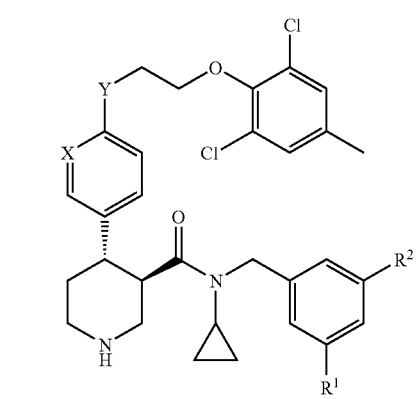

and pharmaceutically acceptable salts thereof, or an optical isomer thereof, wherein
X is N or CH;
Y is O, $CH_2$, or a bond;

$R^1$ is
- —$(CH_2)_{1-3}OR^4$, or
- —$O(CH_2)_{1-2}OR^4$;

$R^2$ is selected from the group consisting of
- —$(CH_2)_{1-5}OR^4$,
- —$O$—$(CH_2)_{2-4}OR^4$,
- —$C(O)R^4$,
- —$OR^4$,
- —$O(CH_2)_{2-4}O$—$(C_3$-$C_8$cycloalkyl), wherein cycloalkyl is unsubstituted or substituted with $C_1$-$C_4$alkyl or $C_1$-$C_4$alkanol,
- —$O(CH_2)_{2-4}NR^4R^5$, and —$O(CH_2)_{1-3}$ $(CH_2)_{1-3}CN$, and 

$R^4$ and $R^5$ are independently $C_1$-$C_6$alkyl unsubstituted or substituted with —OH or $CF_3$.

DETAILED DESCRIPTION OF THE DISCLOSURE

The compounds of Formula I above, and pharmaceutically acceptable salts thereof, are renin inhibitors. The compounds are useful for inhibiting renin and treating conditions such as hypertension.

In one embodiment of the invention, $R^1$ is —$(CH_2)_3OCH_3$, —$(CH_2)_2OCH_3$ or —$O(CH_2)_2OCH_3$ and all other variables are as previously defined.

In one embodiment of the invention, Y is O and all other variables are as previously defined.

In another embodiment of the invention, $R^2$ is selected from the group consisting of
- —$(CH_2)_3OR^4$,
- —$O$—$(CH_2)_2OR^4$,
- —$C(O)R^4$,
- —$OR^4$,
- —$O(CH_2)_2O$—$(C_3$-$C_8$cycloalkyl), wherein cycloalkyl is unsubstituted or substituted with $C_1$-$C_4$alkyl or $C_1$-$C_4$alkanol,
- —$O(CH_2)_2NR^4R^5$, and —$OCH_2$ $CH_2CN$, 

and all other variables are as previously defined.

In another embodiment, $R^2$ is selected from the group consisting of
- —$(CH_2)_3OCH_3$,
- —$O(CH_2)_2OCH_3$,
- —$C(O)CH_3$,
- —$OCH_2C(CH_3)_2OH$,
- —$O(CH_2)_2OCH_2CF_3$,
- —$O(CH_2)_2OCH_3$,
- —$O(CH_2)_2N(CH_3)_2$, —$O(CH_2)_2O$—, —$OCH_2$⸺$CH_2OH$, and 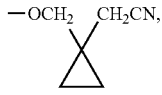

—$OCH_2$ $CH_2CN$, and all other variables are as previously defined.

In another embodiment of the invention, $R^4$ and $R^5$ are independently selected from the group consisting of —$CH_3$, —$CH_2CF_3$, and —$(CH_2)C(CH_3)_2OH$, and all other variables are as previously defined.

Specific examples of compounds of formula I, and pharmaceutically acceptable salts thereof, include
(3R,4S)-N-Cyclopropyl-4-{4-[2-(2,6-dichloro-4-methylphenoxy)ethoxy]phenyl}-N-[3-(2-methoxyethoxy)-5-(3-methoxypropyl)benzyl]piperidine-3-carboxamide,
(3R,4S)-N-Cyclopropyl-4-{6-[2-(2,6-dichloro-4-methylphenoxy)ethoxy]pyridin-3-yl}-N-[3-(2-methoxyethoxy)-5-(3-methoxypropyl)benzyl]piperidine-3-carboxamide,
(3R,4S)-N-Cyclopropyl-4-{4-[2-(2,6-dichloro-4-methylphenoxy)ethoxy]phenyl}N-[3-[2-(dimethylamino)ethoxy]-5-(3-methoxypropyl)benzyl]piperidine-3-carboxamide,
(3R,4S)-N-Cyclopropyl-N-[3-[2-(cyclopropyloxy)ethoxy]-5-(3-methoxypropyl)-benzyl]-4-{4-[2-(2,6-dichloro-4-methylphenoxy)ethoxy]phenyl}piperidine-3-carboxamide,
(3R,4S)-N-Cyclopropyl-4-{4-[2-(2,6-dichloro-4-methylphenoxy)ethoxy]phenyl}-N-{3-(3-methoxypropyl)-5-[2-(2,2,2-trifluoroethoxy)ethoxy]benzyl}piperidine-3-carboxamide,
(3R,4S)-N-Cyclopropyl-4-{4-[2-(2,6-dichloro-4-methylphenoxy)ethoxy]phenyl}-N-[3-(2-hydroxy-2-methylpropoxy)-5-(3-methoxypropyl)benzyl]piperidine-3-carboxamide,
(3R,4S)-N-[3-{[1-(Cyanomethyl)cyclopropyl]methoxy}-5-(3-methoxypropyl)benzyl]-N-cyclopropyl-4-{4-[2-(2,6-dichloro-4-methylphenoxy)ethoxy]phenyl}piperidine-3-carboxamide,
(3R,4S)-N-Cyclopropyl-4-{4-[2-(2,6-dichloro-4-methylphenoxy)ethoxy]phenyl}-N-[3-{[(1R,2R)-2-(hydroxymethyl)cyclopropyl]methoxy}-5-(3-methoxypropyl)benzyl]-piperidine-3-carboxamide,
(3R,4S)-N-[3-Acetyl-5-(3-methoxypropyl)benzyl]-N-cyclopropyl-4-{4-[2-(2,6-di-chloro-4-methylphenoxy)ethoxy]phenyl}piperidine-3-carboxamide,
(3R,4S)-N-Cyclopropyl-4-{4-[2-(2,6-dichloro-4-methylphenoxy)ethoxy]phenyl}-N-[3-(2-methoxyethoxy)-5-(2-methoxyethyl)benzyl]piperidine-3-carboxamide,
(3R,4S)-N-[3,5-Bis(3-methoxypropyl)benzyl]-N-cyclopropyl-4-{4-[2-(2,6-dichloro-4-methylphenoxy)ethoxy]phenyl}piperidine-3-carboxamide, and
(3R,4S)-N-[3,5-Bis(2-methoxyethoxy)benzyl]-N-cyclopropyl-4-{4-[2-(2,6-dichloro-4-methylphenoxy)ethoxy]phenyl}piperidine-3-carboxamide.

The present invention also encompasses a pharmaceutical formulation comprising a pharmaceutically acceptable carrier and the compound of Formula I or a pharmaceutically acceptable crystal form or hydrate thereof. A preferred embodiment is a pharmaceutical composition of the compound of Formula I, comprising, in addition, a second agent.

The compounds of the present invention may have chiral centers, e.g. one chiral center (providing for two stereoisomers, (R) and (S)), or two chiral centers (providing for up to four stereoisomers, (R,R), (S,S), (R,S), and (S,R)). This invention includes all of the optical isomers and mixtures thereof. Unless specifically mentioned otherwise, reference to one isomer applies to any of the possible isomers. Whenever the isomeric composition is unspecified, all possible isomers are included.

Tautomers of compounds defined in Formula I are also included within the scope of the present invention. For example, compounds including carbonyl —CH$_2$C(O)— groups (keto forms) may undergo tautomerism to form hydroxyl —CH=C(OH)— groups (enol forms). Both keto and enol forms are included within the scope of the present invention.

In addition compounds with carbon-carbon double bonds may occur in Z- and E-forms with all isomeric forms of the compounds being included in the present invention.

List of Abbreviations:
ABTS 2,2'-Azino-bis(3-ethylbenzthiazoline-6-sulfonic Acid) 2NH$_3$
Ac acetyl
BSA bovine serum albumin
DCM Dichloromethane
DIBAL diisobutylaluminum hydride
DIBAL-H diisobutylaluminum hydride
DME dimethoxyethane
DMF dimethylformamide
DMSO dimethylsulfoxide
EDTA ethylenediaminetetraacetic acid
EIA enzyme immunoassay
Et$_2$O Diethyl ether
HATU O-(7-azabenzotriazol-1-yl)-N,N,N',N'-tetramethyluronium hexafluorophosphate
HPLC high-pressure liquid chromatography
NMR nuclear magnetic resonance
PBS phosphate-buffered saline
THF tetrahydrofuran
TLC thin layer chromatography Embodiments of the method of the present invention include those in which the compound of Formula I administered to the subject is as defined in the compound embodiments, classes and sub-classes set forth above.

As used herein except where noted, "alkyl" is intended to include both branched- and straight-chain saturated aliphatic hydrocarbon groups, and is intended to include the cyclic group cycloalkyl, including all isomers, having the specified number of carbon atoms. The term "cycloalkyl" means carbocycles containing no heteroatoms. Examples of cycloalkyl include cyclopropyl, cyclobutyl, cyclopentyl, cyclohexyl. Commonly used abbreviations for alkyl groups are used throughout the specification, e.g. methyl may be represented by "Me" or CH$_3$, ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-6}$ alkyl" (or "C$_1$-C$_6$ alkyl") for example, means linear or branched chain alkyl groups, including all isomers, having the specified number of carbon atoms. C$_{1-6}$ alkyl includes all of the hexyl alkyl and pentyl alkyl isomers as well as n-, iso-, sec- and t-butyl, n- and isopropyl, ethyl and methyl. "C$_{1-4}$ alkyl" means n-, iso-, sec- and t-butyl, n- and isopropyl, ethyl and methyl. The term "alkylene" refers to both branched- and straight-chain saturated aliphatic hydrocarbon groups, including all isomers, having the specified number of carbons, and having two terminal end chain attachments. For illustration, the term "unsubstituted A-C$_4$alkylene-B" represents A-CH$_2$—CH$_2$—CH$_2$—CH$_2$—B. The term "alkoxy" represents a linear or branched alkyl group of indicated number of carbon atoms attached through an oxygen bridge. The term "alkanol" in the definition of variable R$^2$ represents a linear or branched alkyl group of indicated number of carbon atoms having at least one hydroxyl substituent, e.g., ethanol, and includes alkanediols and alkanetriols, and attached to the cycloalkyl ring by a carbon-carbon bond.

Structural representations of compounds having substituents terminating with a methyl group may show such terminations as

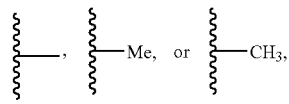

i.e., these have equivalent meaning.

Unless otherwise specifically noted as only "unsubstituted" or only "substituted", alkyl and cycloalkyl are unsubstituted or substituted with 1 to 3 substituents on each carbon atom, with —OH, —CF$_3$, C$_1$-C$_4$alkyl or C$_1$-C$_4$alkanol.

The term "halogen" (or "halo") refers to fluorine, chlorine, bromine and iodine (alternatively referred to as fluoro (F), chloro (Cl), bromo (Br), and iodo (I)).

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

Pharmaceutically acceptable salts include both the metallic (inorganic) salts and organic salts; a list of which is given in *Remington's Pharmaceutical Sciences,* 17th Edition, pg. 1418 (1985). It is well known to one skilled in the art that an appropriate salt form is chosen based on physical and chemical stability, flowability, hydro-scopicity and solubility. As will be understood by those skilled in the art, pharmaceutically acceptable salts include, but are not limited to salts of inorganic acids such as hydrochloride, sulfate, phosphate, diphosphate, hydrobromide, and nitrate or salts of an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with secondary amines). Preferred salts of this invention for the reasons cited above include potassium, sodium, calcium and ammonium salts. Also included within the scope of this invention are crystal forms, hydrates and solvates of the compounds of Formula I.

The compounds of Formula I can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Certain of the compounds employed in the present invention carry an acidic moiety (e.g., —COOH or a phenolic group), in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The invention relates to a method for the treatment and/or prophylaxis of diseases which are related to hypertension, congestive heart failure, pulmonary hypertension, systolic hypertension, renal insufficiency, renal ischemia, renal failure, renal fibrosis, cardiac insufficiency, cardiac hypertrophy, cardiac fibrosis, myocardial ischemia, cardiomyopathy, glomerulonephritis, renal colic, complications resulting from diabetes such as nephropathy, vasculopathy and neuropathy, glaucoma, elevated intra-ocular pressure, atherosclerosis, restenosis post angioplasty, complications following vascular or cardiac surgery, erectile dysfunction, hyperaldosteronism, lung fibrosis, scleroderma, anxiety, cognitive disorders, complications of treatments with immunosuppressive agents, and other diseases known to be related to the renin-angiotensin system, which method comprises administrating a compound as defined above to a human being or animal.

In another embodiment, the invention relates to a method for the treatment and/or prophylaxis of diseases which are related to hypertension, congestive heart failure, pulmonary hypertension, renal insufficiency, renal ischemia, renal failure, renal fibrosis, cardiac insufficiency, cardiac hypertrophy, cardiac fibrosis, myocardial ischemia, cardiomyopathy, complications resulting from diabetes such as nephropathy, vasculopathy and neuropathy.

In another embodiment, the invention relates to a method for the treatment and/or prophylaxis of diseases, which are associated with a dysregulation of the renin-angiotensin system as well as for the treatment of the above-mentioned diseases.

The invention also relates to the use of compounds of formula (I) for the preparation of a medicament for the treatment and/or prophylaxis of the above-mentioned diseases.

Compounds of formula (I) or the above-mentioned pharmaceutical compositions are also of use in combination with other pharmacologically active compounds comprising ACE-inhibitors, neutral endopeptidase inhibitors, angiotensin II receptor antagonists, endothelin receptors antagonists, vasodilators, calcium antagonists, potassium activators, diuretics, sympatholitics, beta-adrenergic antagonists, alpha-adrenergic antagonists or with other drugs beneficial for the prevention or the treatment of the above-mentioned diseases.

The term "administration" and variants thereof (e.g., "administering" a compound) in reference to a compound of Formula I mean providing the compound or a prodrug of the compound to the individual in need of treatment or prophylaxis. When a compound of the invention or a prodrug thereof is provided in combination with one or more other active agents (e.g., an agent such as angiotensin II receptor antagonist, ACE inhibitor, or other active agent which is known to reduce blood pressure), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit renin and thereby elicit the response being sought (i.e., an "inhibition effective amount"). When the active compound (i.e., active ingredient) is administered as the salt, references to the amount of active ingredient are to the free form (i.e., the non-salt form) of the compound.

In a preferred embodiment, this amount is comprised between 1 mg and 1000 mg per day. In a particularly preferred embodiment, this amount is comprised between 1 mg and 500 mg per day. In a more particularly preferred embodiment, this amount is comprised between 1 mg and 200 mg per day.

In the method of the present invention (i.e., inhibiting renin), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990.

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2.sup.nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes and examples are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specifically stated otherwise, the experimental procedures were performed under the following conditions. Evaporation of solvent was carried out using a rotary evaporator under reduced pressure (600-4000 pascals: 4.5-30 mm Hg) with a bath temperature of up to 60° C. Reactions are typically run under nitrogen atmosphere at ambient temperature if not otherwise mentioned. Anhydrous solvent such as THF, DMF, Et$_2$O, DME and Toluene are commercial grade. Reagents are commercial grade and were used without further purification. Flash chromatography is run on silica gel (230-400 mesh). The course of the reaction was followed by either thin layer chromatography (TLC) or nuclear magnetic resonance (NMR) spectrometry and reaction times given are for illustration only. The structure and purity of all final products were ascertained by TLC, mass spectrometry, $^1$H NMR and high-pressure liquid chromatography (HPLC). Chemical symbols have their usual meanings. The following abbreviations have also been used: v (volume), w (weight), b.p. (boiling point), m.p. (melting point), L (liter(s)), mL (milliliter(s)), g (gram(s)), mg (milligram(s)), mol (mole(s)), mmol (millimole(s)), eq. (equivalent(s)). Unless otherwise specified, all variables mentioned below have the meanings as provided above.

Compounds of the present invention can be prepared according to the following general methods as exemplified in Scheme 1. For example, palladium-medium Suzuki coupling between triflate H and boronic acid III can provide α,β-unsaturated ester IV. Reduction of the alkene group in IV can be accomplished using reducing agents such as magnesium. The resulting saturated piperidine V are obtained as a mixture of cis- and trans-diastereomers, which can be equilibrated to the trans-diastereomer VI by refluxing in ethanol in presence of sodium ethoxide. Saponification of ester VI and coupling of the resulting acid VII with amine VIII will provide piperidine IX. R$^2$ groups on aminoamide IX can be further functionalized to R$^3$, affording piperidine XI. Finally, removal of the protecting group can provide the desired piperidine X and XII. X, Y, R$^1$, and R$^2$ are as described above, and R$^3$ is independently defined as R$^2$ above. In the scheme, deprotection of IX forms X, and modification of R$^2$ in IX to R$^3$ in XI independently defined as R$^2$ above, followed by deprotection, forms XII.

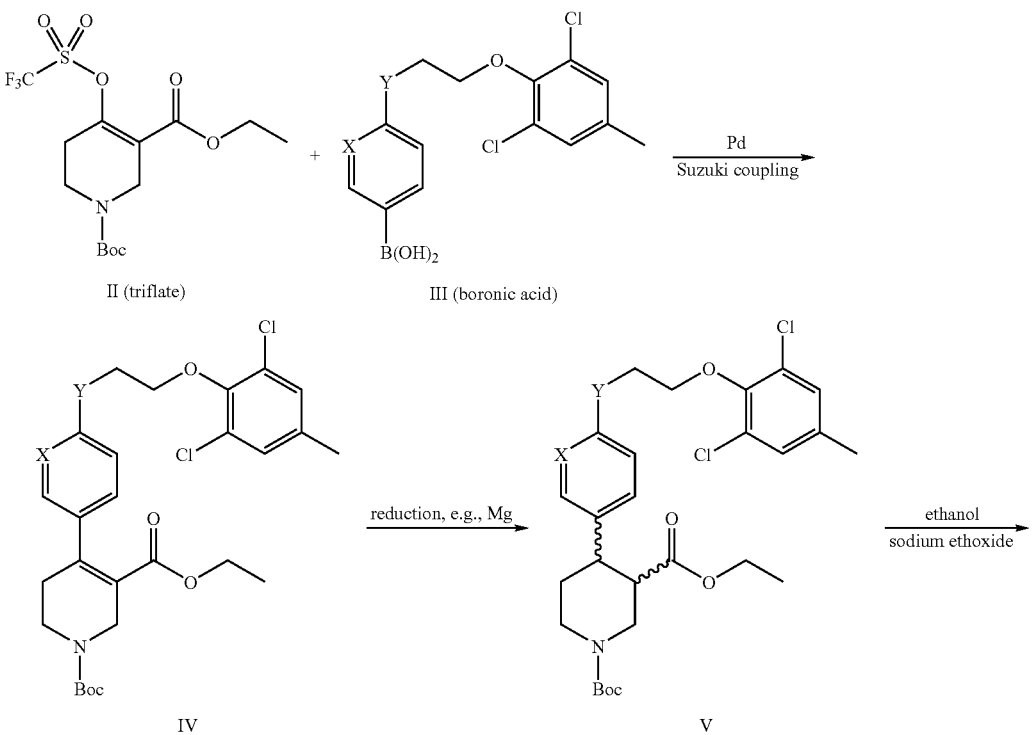

-continued
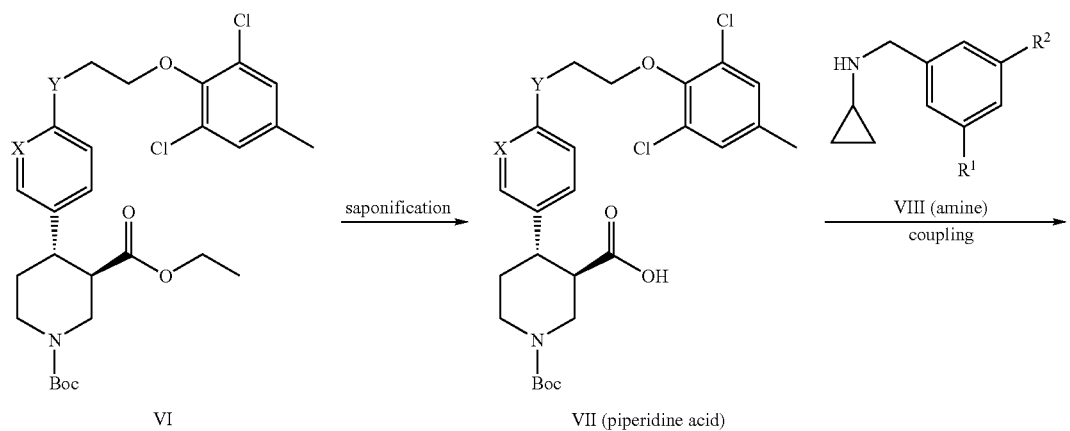
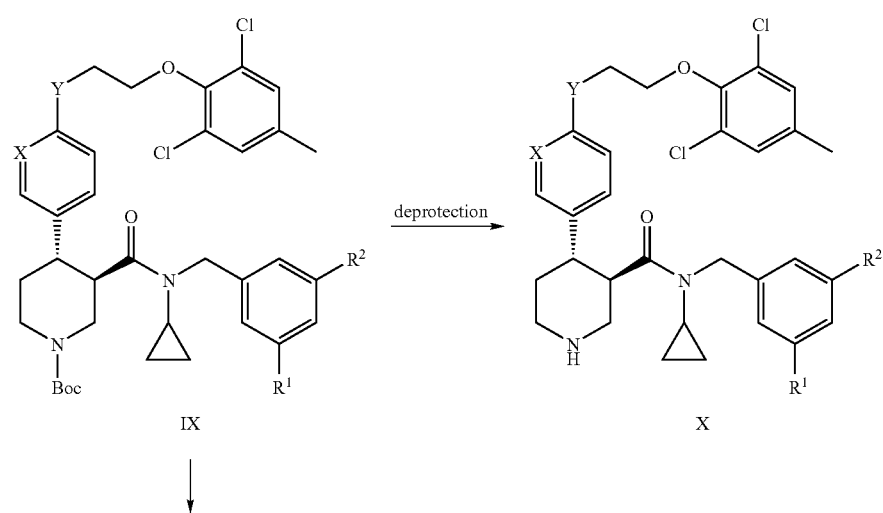
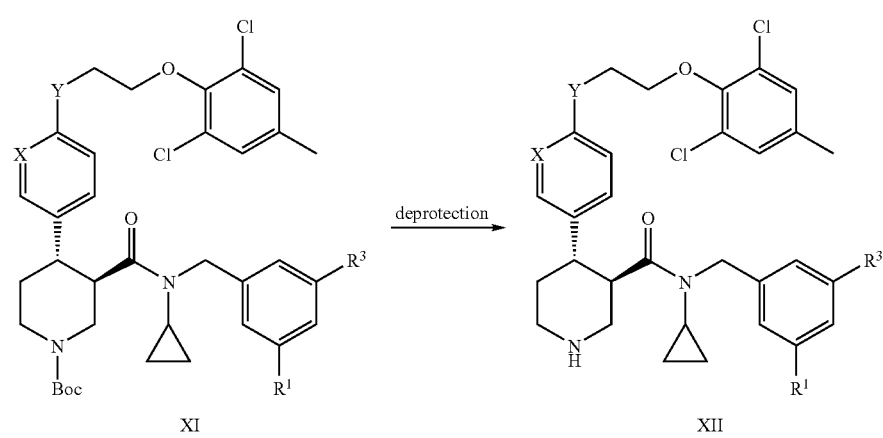

Preparation of Triflates (II in Scheme 1)

| Compound | Structure |
|---|---|
| Triflate 1 | (structure shown: F₃C-SO₂-O- attached to tetrahydropyridine with ethyl ester and N-Boc) |

Triflate 1

Step 1: 1-tert-Butyl 3-ethyl 4-oxopiperidine-1,3-dicarboxylate

To a solution of ethyl 4-oxopiperidine-3-carboxylate hydrogen chloride (1 eq.) in tert-butyl methyl ether (0.85 M) at 0° C. was added di-tert-butyl dicarbonate (1.5 eq.) and 1N aqueous NaOH (1.5 eq.). The reaction was warmed to rt and stirred for 18 h. The reaction was neutralized with 10% aqueous HCl and extracted with ether. The combined organic extracts were washed with brine, dried over MgSO$_4$, and concentrated in vacuo to afford the title compound as a solid.

Step 2: 1-tert-Butyl-3-ethyl-4-{[(trifluoromethyl)sulfonyl]oxy}-5,6-dihydropyridine-1,3(2H)-dicarboxylate To a solution of 1-tert-butyl 3-ethyl 4-oxopiperidine-1,3-dicarboxylate (1 eq.) from the previous step in THF (0.2 M) at 0° C. was added NaH (1 eq.) portionwise. After stirring for 5 min, 1,1,1-trifluoro-N-phenyl-N-[(trifluoromethyl)sulfonyl]-methanesulfonamide (1.05 eq.) was added and the reaction was stirred for 20 h at rt. The reaction mixture was quenched with saturated aqueous NH$_4$Cl solution and extracted with ether. The combined organic extracts were washed with brine, dried over MgSO$_4$, and concentrated in vacuo. The crude mixture was purified by flash column chromatography (SiO$_2$, 10%→15% EtOAc in Hex) to afford triflate 1 compound as a yellow oil.

Preparation of Boronic Acids (III in Scheme 1)

| Compound | Structure |
|---|---|
| Boronic acid 1 | (structure shown: 2,6-dichloro-4-methylphenyl ether linked via -OCH₂CH₂O- to 4-(B(OH)₂)phenyl) |

Boronic Acid 1

Step 1: 1,3-Dichloro-2-(2-chloroethoxy)-5-methylbenzene

To a solution of 4-bromophenol (1 eq.) in dichloroethane/water (4:1 v/v, 0.38 M) was added 10 N NaOH (5 eq.) and catalytic amount of tetrabutylammonium hydrogen sulfate (2 mol %). The reaction was refluxed for 16 h. The aqueous phase was extracted with dichloroethane. The combined organic extracts were washed with saturated aqueous NH$_4$Cl, dried over Na$_2$SO$_4$, and concentrated in vacuo. The residue was suspended in heptane and filtered to give the title compound as a white solid.

Step 2: 2-[2-(4-Bromophenoxy)ethoxy]-1,3-dichloro-5-methylbenzene 1,3-Dichloro-2-(2-chloroethoxy)-5-methylbenzene (1.05 eq.) from the previous step and potassium carbonate (1.1 eq.) were dissolved in DMF (0.5 M) and heated to 100° C. A solution of 2,6-dichloro-4-methylphenol (1 eq.) in DMF was added dropwise over 1 h (final concentration 0.38M). The reaction was stirred at 100° C. for 2 h. After cooling to 40° C., equal volume of water was added to the reaction. The resulting precipitate was filtered and washed extensively with DMF and water. The solids were dried over a steam of air for 3 days to afford the title compound.

Step 3: {4-[2-(2,6-Dichloro-4-methylphenoxy)ethoxy]phenyl}boronic acid

To a solution of 2-[2-(4-bromophenoxy)ethoxy]-1,3-dichloro-5-methylbenzene (1 eq.) from the previous step in THF (0.2 M) at −78° C. was added nBuLi (1.1 eq.) dropwise (internal temperature kept below −70° C.). After stirring for 30 min, triisopropyl borate (2 eq.) was added dropwise (internal temperature kept below −70° C.) and the reaction was slowly warmed to rt over 1 h. The solvent was concentrated in vacuo, and 1 N NaOH was added carefully. After stirring for 15 min, the aqueous solution was extracted with EtOAc. The combined organic extracts were washed with brine, dried over MgSO$_4$, and concentrated in vacuo. The product was stirred in hot DCM/Hex (1:1 v/v) and filtered to give boronic acid 1 compound as a white solid.

Preparation of Piperidine Acids (VII in Scheme 1)

| Compound | Structure |
|---|---|
| Piperidine acid 1 | (structure shown: 2,6-dichloro-4-methylphenyl-O-CH₂CH₂-O-phenyl attached to piperidine bearing COOH and N-Boc) |

-continued

| Compound | Structure |
|---|---|
| Piperidine acid 2 | (structure shown) |

Piperidine acid 1

Step 1: 1-tert-Butyl 3-ethyl-4-{4-[2-(2,6-dichloro-4-methylphenoxy)ethoxy]phenyl}-5,6-dihydropyridine-1,3(2H)-dicarboxylate Triflate 1 (1 eq.) and boronic acid 1 (1 eq.) were dissolved in 2 N aqueous $Na_2CO_3$/n-propanol (1:4 v/v, 0.2 M). The reaction vessel was degassed and flushed with nitrogen gas. $Pd(dppf)Cl_2$ dichloromethane adduct (5 mol %) was added and the reaction was heated to 80° C. for 5 h. The reaction was cooled to rt and diluted with EtOAc. The resulting precipitate was filtered thru a pad of silica, washing with additional EtOAc. The filtrate was concentrated in vacuo. The crude product was purified by flash column chromatography ($SiO_2$, 12.5% EtOAc/Hex) to give the title compound as a yellow oil.

Step 2: 1-tert-Butyl 3-ethyl 4-{4-[2-(2,6-dichloro-4-methylphenoxy)ethoxy]phenyl}-piperidine-1,3-dicarboxylate To a solution of 1-tert-butyl-3-ethyl-4-{4-[2-(2,6-dichloro-4-methylphenoxy)-ethoxy]phenyl}-5,6-dihydropyridine-1,3(2H)-dicarboxylate (1 eq.) from the previous step in methanol (0.2 M) at rt under nitrogen atmosphere was added magnesium turnings (2 eq.). The reaction was stirred vigorously until a gentle reflux of solvent was achieved. After stirring for 1 hr, more magnesium turnings (1 eq.) were added. After another 1.5 h, more magnesium turnings (0.5 eq.) were added. After another 2 h, reaction was quenched with saturated aqueous $NH_4Cl$ solution. The aqueous phase was extracted with ether. The combined organic extracts were washed with brine, dried over anhydrous $MgSO_4$, and concentrated in vacuo to afford a yellow oil that contained 1:1 mixture of cis- and trans-isomers. The mixture of cis- and trans-isomers was dissolved in absolute ethanol under nitrogen atmosphere. A solution of sodium ethoxide in ethanol (prepared by dissolving 1.2 eq. of sodium in absolute ethanol) was added, and the reaction was refluxed for 4 h. After cooling to rt, the reaction was diluted with ether and quenched with saturated aqueous $NH_4Cl$ solution. The aqueous phase was extracted with ether. The combined organic extracts were washed with water, brine, dried over $MgSO_4$, and concentrated in vacuo. The crude product was purified by flash column chromatography ($SiO_2$, 12.5% EtOAc/Hex) to afford the title compound as a yellow oil that consisted of only the trans-diastereomer.

Step 3: 1-tert-Butyl 3-ethyl (3R,4S)-4-{4-[2-(2,6-dichloro-4-methylphenoxy)ethoxy]-phenyl}piperidine-1,3-dicarboxylate Racemic trans-1-tert-butyl 3-ethyl 4-{4-[2-(2,6-dichloro-4-methylphenoxy)-ethoxy]phenyl}-piperidine-1,3-dicarboxylate was resolved by a Chiral Pak AD preparative column (15% EtOH in Hex) to afford two enantiomers. 1-tert-Butyl 3-ethyl (3R,4S)-4-{4-[2-(2,6-dichloro-4-methylphenoxy)ethoxy]-phenyl}piperidine-1,3-dicarboxylate was eluted as the slower enantiomer (retention time=26.5 min).

Step 4: (3R,4S)-1-(tert-Butoxycarbonyl)-4-{4-[2-(2,6-dichloro-4-methylphenoxy)-ethoxy]phenyl}piperidine-3-carboxylic acid To a solution of 1-tert-butyl-3-ethyl-(3R,4S)-4-{4-[2-(2,6-dichloro-4-methyl-phenoxy)ethoxy]-phenyl}piperidine-1,3-dicarboxylate (1 eq.) in ethanol (0.1 M) was added 10 N aqueous NaOH (3 eq.) and refluxed for 18 h. After cooling to rt, the reaction mixture was diluted with EtOAc and quenched with 1 N HCl (until pH <1). The aqueous phase was extracted with EtOAc. The combined organic extracts were washed with brine, dried over anhydrous $MgSO_4$, and concentrated in vacuo to afford piperidine acid 1 compound as a white foam. Piperidine Acid 2

Step 1: 4-{4-[2-(tert-Butyldimethylsilanyloxy) ethoxy]phenyl}-5,6-dihydro-2H-pyridine-1,3-dicarboxylic acid 1-tert-butyl ester 3-methyl ester To a sol. of 4-[2-(tert-butyldimethylsilanyloxy)ethoxy] bromobenzene (WO 03/093267, 7.95 g, 24 mmol) in THF (200 mL) at −78° C. was added BuLi (1.6M in hexane, 17.12 mL, 27.4 mmol). The sol. was stirred at −78° C. for 30 min, then $ZnCl_2$ (1M in THF, 30 mL, 30 mmol) was added. The resulting sol. was allowed to warm to rt, and 4-trifluoromethanesulfonyloxy-5,6-dihydro-2H-pyridine-1,3-dicarboxylic acid 1-tert-butyl ester 3-methyl ester (WO 2004/002957, 7.79 g, 20 mmol) in THF (20 mL) and $Pd(PPh_3)_4$ (0.69 g, 0.60 mmol) were added. The reaction mixture was heated to 50° C. for 1 h, and stirred 16 h at rt. The mixture was cooled to 0° C., and aq. sat. $NH_4Cl$ was added. EtOAc was added, and the org. phase was washed with brine, dried over $MgSO_4$, filtered, and the solvents were removed under reduced pressure. Purification of the residue by FC (EtOAc/heptane 2:8→1:0) yielded the title compound (8.1 g, 82%). LC-MS: $t_R$=1.23 min, ES+: 506.47.

Step 2: 4-{4-[2-(tert-Butyldimethylsilanyloxy) ethoxy]phenyl}piperidine-1,3-dicarboxylic acid 1-tert-butyl ester 3-methyl ester Mg (1.40 g, 58 mmol) was added to a sol. of compound 4-{4-[2-(tert-Butyldimethylsilanyloxy)ethoxy]phenyl}-5,6-dihydro-2H-pyridine-1,3-dicarboxylic acid 1-tert-butyl ester 3-methyl ester (8.10 g, 17 mmol) in MeOH (40 mL) under Ar. The mixture was stirred for 1 h while maintaining the temperature below 30° C. Aq. 1M HCl (115 mL, 115 mmol) was added dropwise and the mixture was stirred for 1 h. The mixture was extracted with EtOAc (2×). The combined org. layers were washed with water, brine, dried over $MgSO_4$, filtered, and the solvents were removed under reduced pressure. Purification of the residue by FC (EtOAc/heptane 2:1) yielded a 2:3 trans/cis mixture of the title compound (7.6 g, 93%). LC-MS: $t_R$=1.23 min, ES+=508.47.

Step 3: 4-[4-(2-Hydroxyethoxy)phenyl]piperidine-1,3-dicarboxylic acid 1-tert-butyl ester 3-methyl ester To a sol. of compound 4-{4-[2-(tert-Butyldimethylsilanyloxy)ethoxy]phenyl}piperidine-1,3-dicarboxylic acid 1-tert-butyl ester 3-methyl ester (7.60 g, 15.4 mmol) in THF (150 mL) at 0° C. and under Ar was added TBAF (4.86 g, 15.4 mmol). After stirring the mixture for 1 h, aq. sat. NH$_4$Cl (100 mL) was added, and the reaction mixture was extracted with EtOAc (2×). The org. layer was washed with water, brine, dried over MgSO$_4$, filtered, and the solvents were removed under reduced pressure. Purification of the residue by FC (EtOAc/heptane 2:1→1:0) yielded the title compound (5.06 g, 87%). LC-MS: $t_R$=0.91 min, ES+=380.30.

Step 4: 4-{4-[2-(2,6-Dichloro-4-methylphenoxy)ethoxy]phenyl}piperidine-1,3-dicarboxylic acid 1-tert-butyl ester 3-methyl ester A mixture of compound 4-[4-(2-Hydroxyethoxy)phenyl]piperidine-1,3-dicarboxylic acid 1-tert-butyl ester 3-methyl ester (5.50 g, 15 mmol), 2,6-dichloro-p-cresol (3.08 g, 18 mmol), azodicarboxylic dipiperidine (7.31 g, 29 mmol) and PBu$_3$ (14 mL, 58 mmol) in toluene (150 mL) was heated to 50° C. for 16 h. The mixture was allowed to cool to rt, filtered, and the precipitate was washed with toluene. The filtrate was diluted with EtOAc, and washed with water (2×) and brine. The org. layer was dried over MgSO$_4$, filtered, and the solvents were removed under reduced pressure. Purification of the crude by FC (EtOAc/heptane 0:1→1:9→2:8) yielded the compound as a colorless oil (7.3 g, 90%). LC-MS: $t_R$=1.18 min, ES+=538.34.

Step 5: (rac.)-(3R*,4S*)-4-{4-[2-(2,6-Dichloro-4-methylphenoxy)ethoxy]phenyl}-piperidine-1,3-dicarboxylic acid 1-tert-butyl ester 3-methyl ester To a sol. of compound 4-{4-[2-(2,6-Dichloro-4-methylphenoxy)ethoxy]phenyl}piperidine-1,3-dicarboxylic acid 1-tert-butyl ester 3-methyl ester (0.21 g, 0.38 mmol) in MeOH (2 mL) under Ar was added NaOMe (6 mg, 0.11 mmol). The mixture was stirred for 3 days at 70° C. Water was added, and the mixture was extracted with EtOAc. The org. phase was washed with brine, dried over MgSO$_4$, filtered, and the solvents were removed under reduced pressure. The title compound (150 mg, 72%) was not further purified. LC-MS: $t_R$=1.18 min, ES+=538.32.

Step 6: (rac.)-(3R*,4S*)-4-{4-[2-(2,6-Dichloro-4-methyl-phenoxy)-ethoxy]-phenyl}-piperidine-1,3-dicarboxylic acid 1-tert-butyl ester To a sol. of compound (rac.)-(3R*,4S*)-4-{4-[2-(2,6-Dichloro-4-methylphenoxy)ethoxy]phenyl}-piperidine-1,3-dicarboxylic acid 1-tert-butyl ester 3-methyl ester (0.15 g, 0.27 mmol) in MeOH (1 mL) was added aq. 1M NaOH (1 mL). The mixture was stirred at 70° C. for 2 h. Water was added, and the mixture was extracted with EtOAc. The org. phase was washed with brine, dried over MgSO$_4$, filtered, and the solvents were removed under reduced pressure. The crude residue was purified on a pad of silica gel to yield the title compound (93 mg, 65%). LC-MS: $t_R$=1.12 min, ES+=524.24.

Step 7: (3R,4S)-4-{4-[2-(2,6-Dichloro-4-methyl-phenoxy)-ethoxy]-phenyl}-piperidine-1,3-dicarboxylic acid 1-tert-butyl ester Compound (rac.)-(3R*,4S*)-4-{4-[2-(2,6-Dichloro-4-methyl-phenoxy)-ethoxy]-phenyl}-piperidine-1,3-dicarboxylic acid 1-tert-butyl ester (4.46 g, 8.5 mmol) was separated using a preparative HPLC equipped with a chiral column as described herein above. An isocratic eluent was applied, consisting of 97% hexane, 3% ethanol, and 0.1% TFA. The piperidine acid 2 compound was obtained (1.35 g, 30%). Analytical chiral HPLC (same eluent as preparative): $t_R$=29.00 min. Resolution by a Chiral Pak AD preparative column (20% EtOH in Hex plus 0.25% formic acid) to afford two enantiomers. (3R,4S)-1-(tert-Butoxycarbonyl)-4-{6-[2-(2,6-dichloro-4-methylphen-oxy)ethoxy]pyridin-3-yl}piperidine-3-carboxylic acid was eluted as the slower enantiomer (retention time=8.54 min).

Preparation of Amines (VIII in Scheme 1)

| Compound | Structure |
| --- | --- |
| Amine 1 | HN-cyclopropyl-CH$_2$-(3,5-disubstituted phenyl with OTBS and (CH$_2$)$_3$OMe) |
| Amine 2 | HN-cyclopropyl-CH$_2$-(3,5-disubstituted phenyl with OCH$_2$CH$_2$OMe and (CH$_2$)$_2$OMe) |
| Amine 3 | HN-cyclopropyl-CH$_2$-(3,5-disubstituted phenyl with (CH$_2$)$_3$OMe and (CH$_2$)$_3$OMe) |
| Amine 4 | HN-cyclopropyl-CH$_2$-(3,5-disubstituted phenyl with two OCH$_2$CH$_2$OMe groups) |

Amine 1

Step 1: 3-Bromo-5-hydroxybenzaldehyde

To a toluene solution (1.6 M) of n-butyl lithium (2.5 M hexane solution, 2.1 eq.) was added at −10° C. n-butyl magnesium chloride (2.0 M THF solution, 0.6 eq.). The reaction mixture was stirred at −10° C. for 30 min before a toluene solution (0.7 M) of 3,5-dibromophenol (1 eq.) was added dropwise at −10° C. over a period of 35 min. After stirring at −10° C. for a further 30 min, the reaction mixture was cooled to −40° C. before DMF (20 eq.) was added dropwise over 20 min. The reaction mixture was then slowly warmed to rt and allowed to stir at rt for 1 h. The reaction was carefully quenched at 0° C. with 10% aqueous HCl and extracted with ether. The combined organic extracts were washed with water and brine and dried over MgSO$_4$. Concentration of the filtrate in vacuo afforded a yellow solid. Recrystallization of the crude product in ether/hexane afforded the title compound as a beige powder.

Step 2: 3-Hydroxy-5-[(1E)-3-methoxyprop-1-en-1-yl]benzaldehyde

3-Bromo-5-hydroxybenzaldehyde (1 eq.) from the previous step and 2-[(1E)-3-methoxyprop-1-en-1-yl]-4,4,5,5-tetramethyl-1,3,2-dioxaborolane (1 eq.) were combined in DMF (0.05 M). To this solution was then added palladium acetate (10 mol %), triphenylphosphine (20 mol %), and sodium carbonate (2 M aqueous solution, 4 eq.). The resulting suspension was heated at 80° C. and stirred for 16 h. The reaction mixture was quenched with 10% aqueous HCl and extracted with ether. The combined organic extracts were washed with water, saturated aqueous NaHCO$_3$ solution, brine, dried over MgSO$_4$, and concentrated in vacuo. The crude product was purified by flash column chromatography (SiO$_2$, 20%→4.33% EtOAc/Hex) to afford the title compound as a yellow oil.

Step 3: 3-{[tert-Butyl(dimethyl)silyl]oxy}-5-[(1E)-3-methoxyprop-1-en-yl]-benzaldehyde 3-Hydroxy-5-[(1E)-3-methoxyprop-1-en-1-yl]benzaldehyde (1 eq.) from the previous step and tert-butylchlorodimethylsilane (1 eq.) were combined in DMF (0.5 M). To this solution was then added imidazole (1.5 eq.), and the reaction mixture was stirred at rt for 16 h. The resulting solution was quenched with water and extracted with ether/hexanes (1:1 v/v). The combined organic extracts were washed with brine, dried over MgSO$_4$, and filtered through a plug of SiO$_2$. Concentration of the filtrate in vacuo afforded the title compound as a pale yellow oil.

Step 4: N-{3-{[tert-Butyl(dimethyl)silyl]oxy}-5-[(1E)-3-methoxyprop-1-en-1-yl]-benzyl}cyclopropanamine To a solution of 3-{[tert-butyl(dimethyl)silyl]oxy}-5-[(1E)-3-methoxyprop-1-en-1-yl]benzaldehyde (1 eq.) from the previous step in DCM was added cyclopropanamine (2 eq.) and magnesium sulfate (1.5 eq.). The resulting suspension was stirred at rt for 12 h. The insolubles were removed via filtration. Concentration of the filtrate in vacuo afforded the crude imine as a yellow oil. This was then taken up in methanol (0.3 M), and then sodium borohydride (1.5 eq.) was added portionwise at 0° C. over 5 min. The reaction mixture was slowly warmed to rt over 1 h and then stirred at it for 2 h. The reaction was slowly quenched with saturated aqueous NaHCO$_3$ solution, and the resulting mixture was extracted with ether. The combined organic extracts were washed with water, brine, dried over MgSO$_4$, and concentrated in vacuo to afford the title compound as a golden, yellow oil.

Step 5: N-[3-{[tert-Butyl(dimethyl)silyl]oxy}-5-(3-methoxypropyl)benzyl]cyclo-propanamine To a solution of N-{3-{[tert-butyl(dimethyl)silyl]oxy}-5-[(1E)-3-methoxyprop-1-en-1-yl]benzyl}cyclopropanamine from the previous step (1 eq.) in EtOAc (0.04 M) was added 10% palladium on activated carbon (10 mol %). The vessel was evacuated and back filled with hydrogen. The reaction suspension was then stirred under a balloon atmosphere of hydrogen for 1.5 h. The reaction was diluted with DCM and filtered through a bed of celite. The insolubles were further washed with EtOAc and methanol. Concentration of the filtrate in vacuo afforded the title compound amine 1 as a colorless oil.

Amine 2

Step 1: 3-(Benzyloxy)-5-(methoxycarbonyl)benzoic acid

To a solution of dimethyl 5-hydroxyisophthalate (1 eq.) in DMF (0.5 M) at 0° C. was added portionwise NaH (1.2 eq.) and stirred for 30 min at 0° C. Benzyl bromide (1.2 eq.) was added and the reaction was stirred at rt for 1.5 h. The reaction was then quenched with water (½ volume), and the resulting precipitate was filtered and washed with hexane. The filtrate was diluted with ether and washed several times with water and brine. The organic extract was dried over MgSO$_4$ and concentrated in vacuo to give a solid which was combined with the filtered precipitate to give dimethyl 5-(benzyloxy) isophthalate. This compound was subsequently dissolved in THF/MeOH (2:1, 0.5 M), and to this solution was added KOH powder. After stirring for 18 h at rt, the reaction was poured into a solution of ether/water. The two layers were separated and the ethereal layer was discarded. The aqueous layer was acidified to pH <1 with 3 N HCl and extracted with EtOAc. The combined organic extracts were dried over MgSO$_4$ and concentrated in vacuo to afford the title compound as a white solid.

Step 2: Methyl 3-(benzyloxy)-5-(hydroxymethyl)benzoate

To a solution of 3-(benzyloxy)-5-(methoxycarbonyl)benzoic acid (1 eq.) from the previous step in THF (0.2 M) at 0° C. was added borane-dimethylsulfide (1.5 eq.) and stirred at rt for 18 h. Additional borane-dimethylsulfide (3 eq.) was added and the reaction was stirred for another 2 h at rt. The reaction was slowly quenched with methanol and then concentrated in vacuo. The residue was diluted with EtOAc and washed with saturated aqueous NaHCO$_3$ solution, and brine. The organic extract was dried over MgSO$_4$ and concentrated in vacuo to give the title compound.

Step 3: Methyl 3-(benzyloxy)-5-formylbenzoate

To a solution of DMSO (2.5 eq.) in DCM at −78° C. was added oxalyl chloride (2.5 eq.). The reaction was stirring at −78° C. for 25 min before adding a solution of methyl 3-(benzyloxy)-5-(hydroxy-5-methyl)benzoate (1 eq.) from the previous step in DCM. After 5 min, triethylamine (5 eq.) was added, and the reaction was warmed to rt over 30 min. The reaction was quenched with 1 N aqueous HCl and extracted with DCM. The combined organic extracts were dried over MgSO$_4$ and concentrated in vacuo. The crude product was purified by flash column chromatography (SiO$_2$, 10% EtOAc in Hex) to afford the title compound as an oil.

Step 4: Methyl 3-(benzyloxy)-5-[2-methoxyvinyl]benzoate

To a solution of (methoxymethyl)(triphenyl)phosphonium chloride (1.5 eq.) in THF (0.1 M) at −78° C. was added n-BuLi (1.5 eq.) dropwise. The reaction was stirred at −78° C. for 30 min and then added a solution of methyl 3-(benzyloxy)-5-formylbenzoate (1 eq.) from the previous step in THF. After stirring at rt for 40 min, the reaction was quenched with saturated aqueous $NH_4Cl$ solution. The aqueous layer was extracted with ether. The combined organic extracts were washed with brine, dried over $MgSO_4$, and concentrated in vacuo. The crude product was purified by flash column chromatography ($SiO_2$, 15% EtOAc in Hex) to afford a mixture of E- and Z-methyl 3-(benzyloxy)-5-[2-methoxyvinyl]benzoate.

Step 5: Methyl
3-hydroxy-5-(2-methoxyethyl)benzoate

To a solution of methyl 3-(benzyloxy)-5-[2-methoxyvinyl]benzoate (1 eq.) from the previous step in ethanol was added 10% palladium on activated carbon (5 mol %). The reaction vessel was evacuated and back-filled with hydrogen twice. After 1 h, more 10% palladium on activated carbon (5 mol %) was added and the reaction was stirred for 18 h. The reaction was diluted with DCM and filtered through a pad of celite. Concentration in vacuo afforded the title compound as an oil.

Step 6: Methyl
3-(2-methoxyethoxy)-5-(2-methoxyethyl)benzoate

To a solution of methyl 3-hydroxy-5-(2-methoxyethyl)benzoate (1 eq.) from the previous step in DMF (0.2 M) was added $Cs_2CO_3$ (2 eq.) and 1-bromo-2-methoxy-ethane (2 eq.). The reaction was heated to 80° C. and stirred for 18 h. After cooling to rt, the reaction was diluted with ether and washed extensively with water and brine. The organic extract was dried over $MgSO_4$ and concentrated in vacuo. The crude product was purified by flash column chromatography ($SiO_2$, 25% EtOAc in Hex) to afford the title compound as an oil.

Step 7:
3-(2-Methoxyethoxy)-5-(2-methoxyethyl)benzaldehyde

To a solution of methyl 3-(2-methoxyethoxy)-5-(2-methoxyethyl)benzoate (1 eq.) from the previous step in THF (0.1 M) at −78° C. was added DIBAL-H (3 eq.). The reaction was warmed to −50° C. for 1 h, and then stirred at 0° C. for an additional 30 min. The reaction was quenched with an aqueous solution of Rochelle's salt and EtOAc. After stirring vigorously at rt for 1 h, the layers separated. The aqueous layer was extracted with EtOAc. The combined organic extracts were washed with brine, dried over $MgSO_4$, and concentrated in vacuo to give [3-(2-methoxyethoxy)-5-(2-methoxyethyl)phenyl]methanol as an oil. This intermediate (1 eq.) was dissolved in DCM and added to a solution of DMSO (2.5 eq.) and oxalyl chloride (2.5 eq.) in DCM, premixed at −78° C. for 25 min. After 5 min, triethylamine (5 eq.) was added, and the reaction was warmed to rt over 30 min. The reaction was quenched with 1 N aqueous HCl and extracted with DCM. The combined organic extracts were dried over $MgSO_4$ and concentrated in vacuo. The crude product was purified by flash column chromatography ($SiO_2$, 30% EtOAc in Hex) to give the title compound as an oil.

Step 8: N-[3-(2-Methoxyethoxy)-5-(2-methoxyethyl)benzyl]cyclopropanamine

To a solution of 3-(2-methoxyethoxy)-5-(2-methoxyethyl)benzaldehyde (1 eq.) from the previous step in DCM (0.1 M) was added cyclopropanamine (2 eq.) and anhydrous $MgSO_4$ (1.5 eq.). The reaction was stirred for 18 h at rt. Filtration and concentration in vacuo afforded the corresponding imine as an oil. This oil was dissolved in methanol (0.1 M), cooled to 0° C., and added sodium borohydride (1.5 eq.) The reaction was stirred at rt for 1.5 h and then quenched with saturated aqueous $NaHCO_3$ solution. The aqueous layer was extracted with EtOAc. The combined organic extracts were washed with brine, dried over $MgSO_4$, and concentrated in vacuo to give the title compound amine 2 as an oil.

Amine 3

Step 1: Methyl 3,5-dibromobenzoate

To a solution of 3,5-dibromobenzoic acid (1 eq.) in ether was added dropwise a solution of diazomethane in ether until gas evolution had ceased. The reaction was stirred for 20 min and concentrated in vacuo to afford the title compound.

Step 2: Methyl
3,5-bis[(1E)-3-methoxyprop-1-en-1-yl]benzoate

To a solution of methyl 3,5-dibromobenzoate (1 eq.) from the previous step in DMF (0.2 M) was added 2-[(1E)-3-methoxyprop-1-en-1-yl]-4,4,5,5-tetramethyl-1,3,2-dioxaborolane (2.1 eq.), palladium acetate (10 mol %), triphenylphosphine (30 mol %), and 2.0 M aqueous sodium carbonate solution (5 eq.). The reaction was heated to 80° C. and stirred for 3 h. After cooling to rt, the reaction was diluted with ether. The organic extract was washed with water, brine, dried over $MgSO_4$, and concentrated in vacuo. The crude product was purified by flash column chromatography ($SiO_2$, 20% EtOAc in Hex) to afford the title compound as an oil.

Step 3: Methyl 3,5-bis(3-methoxypropyl)benzoate

To a solution of methyl 3,5-bis[(1E)-3-methoxyprop-1-en-1-yl]benzoate (1 eq.) from the previous step in refluxing toluene was added benzenesulfonohydrazide (5 eq) in five portions over 2 h. The reaction was stirring as reflux for 18 h. After cooling to rt, the reaction was diluted with ether. The organic extract was washed with 1 N aqueous HCl, brine, dried over $MgSO_4$, and concentrated in vacuo. The crude product was purified by flash column chromatography ($SiO_2$, 20% EtOAc in Hex) to afford the title compound as an oil.

Step 4: 3,5-Bis(3-methoxypropyl)benzoic acid

To a solution of methyl 3,5-bis(3-methoxypropyl)benzoate (1 eq.) from the previous step in THF/MeOH (2:1 v/v, 0.1 M) was added 2 M aqueous NaOH (2 eq.). After stirring at rt for 72 h, the reaction was diluted with EtOAc. The organic extract was washed with 10% aqueous HCl solution, brine, dried over $MgSO_4$, and concentrated in vacuo to afford the title compound as an oil.

Step 5:
N-Cyclopropyl-3,5-bis(3-methoxypropyl)benzamide

To a solution of 3,5-bis(3-methoxypropyl)benzoic acid (1 eq.) from the previous step in DCM (0.1 M) was added cyclopropanamine (1.3 eq.), o-benzotriazol-1-yl-N,N,N',N'-tetramethyluronium hexafluorophosphate (aka. HATU, 1.5 eq.), and triethylamine (3 eq.). After stirring at rt for 18 h, the reaction was diluted with EtOAc. The organic extract was washed with 10% aqueous HCl solution, brine, dried over MgSO$_4$, and concentrated in vacuo. The crude product was purified by flash column chromatography (SiO$_2$, 50%→>70% EtOAc in Hex) to afford the title compound as an oil.

Step 6:
N[3,5-Bis(3-methoxypropyl)benzyl]cyclopropanamine

To a solution of N-cyclopropyl-3,5-bis(3-methoxypropyl) benzamide (1 eq.) from the previous step in THF (0.18 M) at 80° C. was added borane-dimethylsulfide (10 eq.). The reaction was distilled to about half volume and heated under reflux for 3 h. Then, the reaction was cooled to rt and slowly quenched with 10% HCl aqueous solution. The reaction was heated to reflex again and stirred for 45 min. After cooling to rt, the reaction was diluted with EtOAc and basified with aqueous NaOH solution (pH >10). The organic extract was washed with saturated aqueous NaHCO$_3$, brine, dried over MgSO$_4$, and concentrated in vacuo. The crude product was purified by flash column chromatography (SiO$_2$, 25% EtOAc in Hex plus 3% Et$_3$N) to afford the title compound amine 3 as an oil.

Amine 4

Step 1: 3,5-Bis(2-methoxyethoxy)benzaldehyde

To a solution of 3,5-dihydroxybenzaldehyde (1 eq.) in DMF (0.36 M) was added cesium carbonate (3 eq.) and 2-bromoethyl methyl ether (5.1 eq.). The reaction was heated to 50° C. and stirred for 18 h. After cooling to ambient temperature, the reaction mixture was diluted with EtOAc/ether (1:1 v/v) and washed with saturated aqueous NH$_4$Cl solution, water, and brine. The organic extract was dried over MgSO$_4$ and concentrated in vacuo. The crude product was purified by flash column chromatography (SiO$_2$, 10%→75% EtOAc in Hex) to afford the title compound as a yellow oil.

Step 2:
N-[3,5-Bis(2-methoxyethoxy)benzyl]cyclopropanamine

To a solution of 3,5-bis(2-methoxyethoxy)benzaldehyde (1 eq.) from the previous step in DCM (0.1 M) was added cyclopropanamine (2 eq.) and anhydrous MgSO$_4$ (2 eq.). The reaction was stirred for 18 h at rt. Filtration and concentration in vacuo afforded the corresponding imine as an oil. This oil was dissolved in methanol (0.1 M), cooled to 0° C., and added sodium borohydride (2 eq.) The reaction was stirred at rt for 3 h and then quenched with 1N aqueous NaOH solution. The aqueous layer was extracted with ether. The combined organic extracts were washed with brine, dried over Na$_2$SO$_4$, and concentrated in vacuo. The crude product was purified by flash column chromatography (SiO$_2$, 20%→40% EtOAc in Hex with 3% Et$_3$N) to afford the title compound amine 4 as a yellow oil.

Compounds of the present invention were prepared according to the following methods.

EXAMPLE 1

(3R,4S)-N-Cyclopropyl-4-{4-[2-(2,6-dichloro-4-methylphenoxy)ethoxy]phenyl}-N-[3-(2-methoxy-ethoxy)-5-(3-methoxypropyl)benzyl]piperidine-3-carboxamide

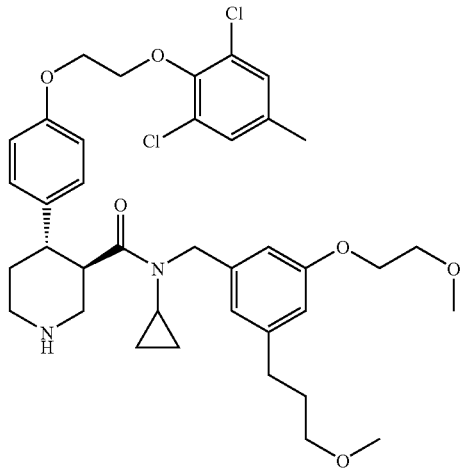

Step 1: tert-Butyl (3R,4S)-3-{[[3-{[tert-butyl(dimethyl)silyl]oxy}-5-(3-methoxy-propyl)benzyl](cyclopropyl)amino]carbonyl}-4-{4-[2-(2,6-dichloro-4-methyl-phenoxy)ethoxy]phenyl}piperidine-1-carboxylate To a solution of (3R,4S)-1-(tert-butoxycarbonyl)-4-{4-[2-(2,6-dichloro-4-methylphenoxy)ethoxy]phenyl}piperidine-3-carboxylic acid (piperidine acid 1) (1 eq) and N-[3-{[tert-Butyl(dimethyl)silyl]oxy}-5-(3-methoxypropyl)benzyl] cyclo-propanamine (amine 1) (1.8 eq.) in DCM (0.15 M) was added HATU (1.5 eq.) and Hunig's base (3 eq.). After stirring for 18 hr at rt, the reaction was diluted with ether. The organic extract was washed three times with 1 N aqueous HCl, water, brine, dried over MgSO$_4$, and concentrated in vacuo. The crude product was purified by flash column chromatography (SiO$_2$, 20% EtOAc in Hex) to afford the title compound as an oil.

Step 2: tert-Butyl (3R,4S)-3-({cyclopropyl[3-hydroxy-5-(3-methoxypropyl)benzyl]-amino}carbonyl)-4-{4-[2-(2,6-dichloro-4-methylphenoxy)ethoxy]phenyl}piperidine-1-carboxylate To a solution of tert-butyl (3R,4S)-3-{[[3-{[tert-butyl(dimethyl)silyl]oxy}-5-(3-methoxypropyl)benzyl](cyclopropyl)amino]carbonyl}-4-{4-[2-(2,6-dichloro-4-methylphenoxy)ethoxy]phenyl}piperidine-1-carboxylate (1 eq.) from the previous step in THF (0.1 M) was added a solution of 1 M tetrabutylammonium fluoride in THF (1.3 eq.). The reaction was stirred at it for 1 h and then concentrated in vacuo. The residue was purified by flash column chromatography (SiO$_2$, 50% EtOAc in Hex) to afford the title compound as a foam.

Step 3: tert-Butyl (3R,4S)-3-({cyclopropyl[3-(2-methoxyethoxy)-5-(3-methoxy-propyl)benzyl] amino}carbonyl)-4-{4-[2-(2,6-dichloro-4-methylphenoxy)ethoxy]-phenyl}piperidine-1-carboxylate To a solution of tert-butyl (3R,4S)-3-({cyclopropyl[3-hydroxy-5-(3-methoxy-propyl)benzyl]amino}carbonyl)-4-{4-

[2-(2,6-dichloro-4-methylphenoxy)ethoxy]-phenyl}piperidine-1-carboxylate (1 eq.) from the previous step in DMF (0.2 M) was added cesium carbonate (1.3 eq.) and 2-bromoethyl methyl ether (1.6 eq.). The reaction was heated to 80° C. and stirred for 3 h. After cooling to rt, the reaction was diluted with EtOAc. The organic extract was washed with water, brine, dried over MgSO$_4$, and concentrated in vacuo. The crude product was purified by flash column chromatography (SiO$_2$, 50%→65% EtOAc in Hex) to afford the title compound as an oil.

Step 4: (3R,4S)-N-Cyclopropyl-4-{4-[2-(2,6-dichloro-4-methylphenoxy)ethoxy]-phenyl}-N-[3-(2-methoxyethoxy)-5-(3-methoxypropyl)benzyl]piperidine-3-carboxamide To a solution tert-butyl (3R,4S)-3-({cyclopropyl[3-(2-methoxyethoxy)-5-(3-methoxypropyl)benzyl]amino}carbonyl)-4-{4-[2-(2,6-dichloro-4-methylphenoxy)-ethoxy]phenyl}piperidine-1-carboxylate (1 eq.) from the previous step in DCM (0.05 M) was added 4 M HCl in dioxane (10 eq.) and stirred at rt for 5 h. The reaction was concentrated in vacuo. The crude product was purified by flash column chromatography (SiO$_2$, 5% [2 M NH$_3$ in MeOH] in DCM) to afford the title compound as a colorless oil. $^1$H NMR (acetone d-6): δ 7.28 (s, 2H), 7.20 (d, 2H), 6.84 (d, 2H), 6.62 (s, 1H), 6.48 (s, 1H), 6.4 (s, 1H), 4.47-4.25 (m, 6H), 4.05 (t, 2H), 3.71 (t, 2H), 3.56 (m, 1H), 3.38 (s, 3H), 3.33 (t, 2H), 3.28 (s, 3H), 3.25 (m, 1H), 3.11 (m, 2H), 2.76 (m, 2H), 2.55 (t, 2H), 2.34 (s, 3H), 2.32 (m, 1H), 1.78 (m, 4H), 0.77 (m, 3H), 0.49 (m, 1H). LRMS [M+H]=699.0

EXAMPLE 2

(3R,4S)-N-Cyclopropyl-4-{6-[2-(2,6-dichloro-4-methylphenoxy)ethoxy]pyridin-3-yl}-N-[3-(2-methoxyethoxy)-5-(3-methoxypropyl)benzyl]piperidine-3-carboxamide

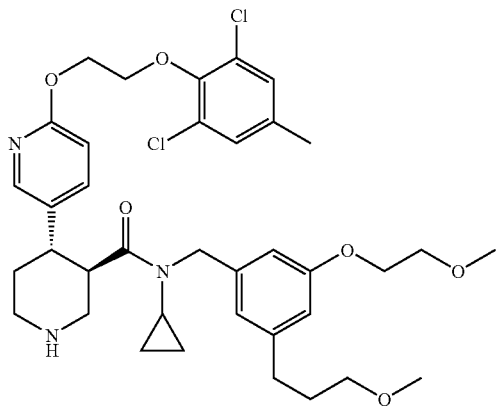

Prepared according to the procedure described in Example 1 but using instead piperidine acid 2 as the starting material. The title compound was a colorless oil. $^1$H NMR (acetone d-6): δ 8.04 (d, 1H), 7.62 (d, 1H), 7.27 (s, 2H), 6.70 (d, 1H), 6.63 (s, 1H), 6.48 (s, 1H), 6.42 (s, 1H), 4.60-4.70 (m, 2H), 4.31-4.41 (m, 4H), 4.05-4.10 (m, 2H), 3.70-3.74 (m, 2H), 3.63 (t, 1H), 3.28-3.38 (m, 9H), 3.11 (m, 2H), 2.70-2.90 (m, 2H), 2.50-2.60 (t, 2H), 2.41-2.45 (m, 1H), 2.33 (s, 3H), 1.70-1.90 (m, 4H), 0.4-0.9 (m, 4H). LRMS [M+H]=700.0

EXAMPLE 3

(3R,4S)-N-Cyclopropyl-4-{4-[2-(2,6-dichloro-4-methylphenoxy)ethoxy]phenyl}-N-[3-[2-(dimethylamino)ethoxy]-5-(3-methoxypropyl)benzyl]piperidine-3-carboxamide

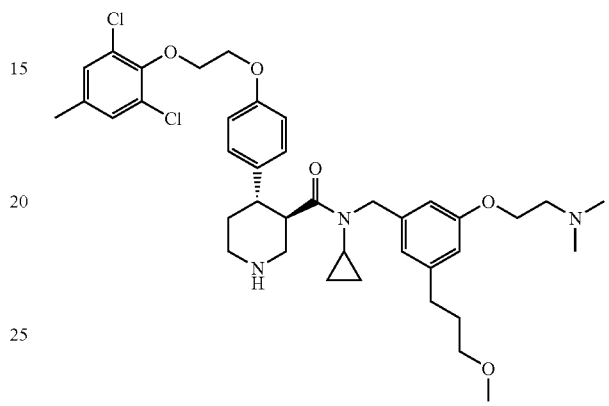

Step 1: tert-Butyl (3R,4S)-3-({cyclopropyl[3-[2-(dimethylamino)ethoxy]-5-(3-methoxypropyl)benzyl]amino}carbonyl)-4-{4-[2-(2,6-dichloro-4-methylphenoxy)-ethoxy]phenyl}piperidine-1-carboxylate To a solution of tert-butyl (3R,4S)-3-({cyclopropyl[3-hydroxy-5-(3-methoxy-propyl)benzyl]amino}carbonyl)-4-{4-[2-(2,6-dichloro-4-methylphenoxy)ethoxy]-phenyl}piperidine-1-carboxylate (1 eq.) from Example 1/Step 2 in DMF was added potassium carbonate (4.4 eq.) and 2-chloro-N,N-dimethylethanamine hydrochloride (2.5 eq.). The reaction was heated to 80° C. and stirred for 4 hr. After cooling to rt, the reaction was diluted with ether. The organic extract was washed with 5% aqueous potassium carbonate solution, brine, dried over MgSO$_4$, and concentrated in vacuo. The crude product was purified by flash column chromatography (SiO$_2$, 2%→5% [2 M NH$_3$ in MeOH] in DCM) to afford the title compound as an oil.

Step 2: (3R,4S)-N-Cyclopropyl-4-{4-[2-(2,6-dichloro-4-methylphenoxy)ethoxy]-phenyl}-N-[3-[2-(dimethylamino)ethoxy]-5-(3-methoxypropyl)benzyl]piperidine-3-carboxamide Prepared according to the procedure described in Example 1/Step 4 but using instead tert-butyl (3R,4S)-3-({cyclopropyl[3-[2-(dimethylamino)ethoxy]-5-(3-methoxypropyl)benzyl]amino}carbonyl)-4-{4-[2-(2,6-dichloro-4-methylphenoxy)-ethoxy]phenyl}piperidine-1-carboxylate from the previous step as the starting material. The title compound was a colorless oil. $^1$H NMR (acetone d-6): δ 7.29 (s, 2H), 7.20 (d, 2H), 6.88 (d, 2H), 6.61 (s, 1H), 6.50 (s, 1H), 6.39 (s, 1H), 4.28-4.42

(m, 6H), 4.00 (t, 2H), 3.56 (dt, 1H), 3.32 (t, 2H), 3.28 (s, 3H), 3.20 (d, 1H), 3.02-3.14 (m, 2H), 2.68-2.85 (m, 3H), 2.66 (t, 2H), 2.52 (t, 2H), 2.29-2.34 (m, 3H), 2.25 (s, 6H), 1.69-1.81 (m, 4H), 0.4-0.9 (m, 4H). LRMS [M+H]=711.9

EXAMPLE 4

(3R,4S)-N-Cyclopropyl-N-[3-[2-(cyclopropyloxy)ethoxy]-5-(3-methoxypropyl)-benzyl]-4-{4-[2-(2,6-dichloro-4-methylphenoxy)ethoxy]phenyl}piperidine-3-carboxamide

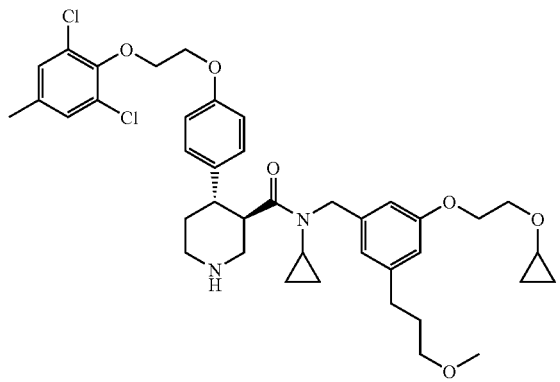

Step 1: tert-Butyl (3R,4S)-3-({cyclopropyl[3-[2-(cyclopropyloxy)ethoxy]-5-(3-methoxypropyl)benzyl]amino}carbonyl)-4-{4-[2-(2,6-dichloro-4-methylphenoxy)-ethoxy]phenyl}piperidine-1-carboxylate To a solution of tert-butyl (3R,4S)-3-({cyclopropyl[3-hydroxy-5-(3-methoxy-propyl)benzyl]-amino}carbonyl)-4-{4-[2-(2,6-dichloro-4-methylphenoxy)ethoxy]-phenyl}piperidine-1-carboxylate (1 eq.) from Example 1/Step 2 in DMF (0.1 M) was added (2-chloroethoxy)cyclopropane (3 eq.) and cesium carbonate (2 eq.). The reaction was heated to 100° C. and stirred for 3 h. After cooling to rt, the reaction was diluted with ether. The organic extract was washed with water, brine, dried over MgSO$_4$, and concentrated in vacuo. The crude product was purified by flash column chromatography (SiO$_2$, 35% EtOAc in Hex) to afford the title compound as an oil.

Step 2: (3R,4S)-N-Cyclopropyl-N-[3-[2-(cyclopropyloxy)ethoxy]-5-(3-methoxy-propyl)benzyl]-4-{4-[2-(2,6-dichloro-4-methylphenoxy)ethoxy]phenyl}piperidine-3-carboxamide Prepared according to the procedure described in Example 1/Step 4 but using instead tert-butyl (3R,4S)-3-({cyclopropyl[3-[2-(cyclopropyloxy)ethoxy]-5-(3-methoxypropyl)benzyl]amino}carbonyl)-4-{4-[2-(2,6-dichloro-4-methylphenoxy)-ethoxy]phenyl}piperidine-1-carboxylate from the previous step as the starting material. The title compound was a colorless oil. $^1$H NMR (acetone d-6): δ 7.29 (s, 2H), 7.20 (d, 2H), 6.84 (d, 2H), 6.60 (s, 1H), 6.48 (s, 1H), 6.40 (s, 1H), 4.30-4.45 (m, 5H), 4.25 (d, 1H), 4.02 (t, 2H), 3.80 (t, 2H), 3.53 (dt, 1H), 3.00-3.42 (m, 9H), 2.70-2.85 (m, 2H), 2.53 (t, 2H), 2.30-2.45 (m, 4H), 1.70-1.85 (m, 4H), 0.4-0.9 (m, 8H). LRMS [M+H]=725.2

EXAMPLE 5

(3R,4S)-N-Cyclopropyl-4-{4-[2-(2,6-dichloro-4-methylphenoxy)ethoxy]phenyl}-N-{3-(3-methoxypropyl)-5-[2-(2,2,2-trifluoroethoxy)ethoxy]benzyl}piperidine-3-carboxamide

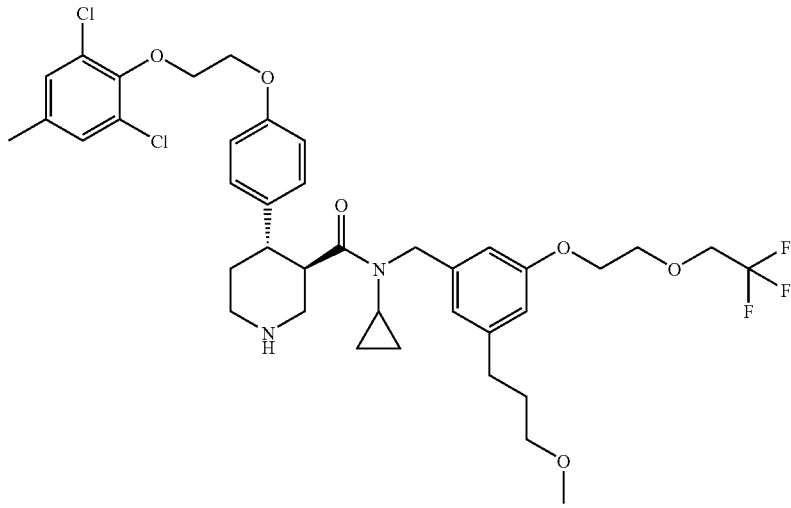

Step 1: 2-(2,2,2-Trifluoroethoxy)ethyl 4-methylbenzenesulfonate

To a solution of 2-(2,2,2-trifluoroethoxy)ethanol (1 eq.) in DCM (0.2 M) was added p-toluenesulfonyl chloride (1.3 eq.) and triethylamine (1.5 eq.). The reaction was stirred at rt for 18 h. The reaction was quenched with saturated NH$_4$Cl aqueous solution and extracted with DCM. The combined organic extracts were dried over MgSO$_4$ and concentrated in vacuo. The crude product was purified by flash column chromatography (SiO$_2$, 30% ether in hexane) to afford the title compound as an oil.

Step 2: tert-Butyl (3R,4S)-3-[(cyclopropyl{3-(3-methoxypropyl)-5-[2-(2,2,2-trifluoro-ethoxy)benzyl}amino)carbonyl]-4-{4-[2-(2,6-dichloro-4-methylphenoxy)-ethoxy]phenyl}piperidine-1-carboxylate To a solution of tert-butyl (3R,4S)-3-({cyclopropyl[3-hydroxy-5-(3-methoxy-propyl)benzyl]-amino}carbonyl)-4-{4-[2-(2,6-dichloro-4-methylphenoxy)ethoxy]phenyl}piperidine-1-carboxylate (1 eq.) from Example 1/Step 2 in DMF (0.1 M) was added 2-(2,2,2-trifluoroethoxy)ethyl 4-methylbenzenesulfonate (3 eq.) from the previous step, cesium carbonate (2 eq.), and sodium iodide (5 mol %). The reaction was heated to 100° C. and stirred for 2.5 h. After cooling to rt, the reaction was diluted with ether. The organic extract was washed with water, brine, dried over MgSO$_4$, and concentrated in vacuo. The crude product was purified by flash column chromatography (SiO$_2$, 40% EtOAc in Hex) to afford the title compound as an oil.

Step 3: (3R,4S)-N-Cyclopropyl-4-{4-[2-(2,6-dichloro-4-methylphenoxy)ethoxy]-phenyl}-N-{3-(3-methoxypropyl)-5-[2-(2,2,2-trifluoroethoxy)ethoxy]benzyl}-piperidine-3-carboxamide Prepared according to the procedure described in Example 1/Step 4 but using instead tert-butyl (3R,4S)-3-[(cyclopropyl{3-(3-methoxypropyl)-5-[2-(2,2,2-trifluoroethoxy)ethoxy]benzyl}amino)carbonyl]-4-{4-[2-(2,6-dichloro-4-methylphenoxy)ethoxy]phenyl}piperidine-1-carboxylate from the previous step as the starting material. The title compound was a colorless oil. $^1$H NMR (acetone d-6): δ 7.30 (s, 2H), 7.20 (d, 2H), 6.85 (d, 2H), 6.65 (s, 1H), 6.50 (s, 1H), 6.41 (s, 1H), 4.35-4.45 (m, 5H), 4.28 (d, 1H), 4.00-4.18 (m, 6H), 3.57 (dt, 1H), 3.35 (t, 2H), 3.29 (s, 3H), 3.00-3.25 (m, 3H), 2.70-2.85 (m, 2H), 2.55 (t, 2H), 2.30-2.40 (m, 4H), 1.70-1.85 (m, 4H), 0.4-0.9 (m, 4H). LRMS [M+H]=768.6

EXAMPLE 6

(3R,4S)-N-Cyclopropyl-4-{4-[2-(2,6-dichloro-4-methylphenoxy)ethoxy]phenyl}-N-[3-(2-hydroxy-2-methylpropoxy)-5-(3-methoxypropyl)benzyl]piperidine-3-carboxamide

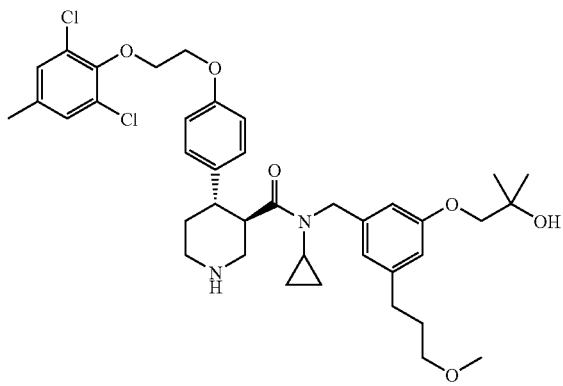

Step 1: tert-Butyl (3R,4S)-3-({cyclopropyl[3-(2-hydroxy-2-methylpropoxy)-5-(3-methoxypropyl)benzyl]amino}carbonyl)-4-{4-[2-(2,6-dichloro-4-methylphenoxy)-ethoxy]phenyl}piperidine-1-carboxylate To a solution of tert-butyl (3R,4S)-3-({cyclopropyl[3-hydroxy-5-(3-methoxy-propyl)benzyl]-amino}carbonyl)-4-{4-[2-(2,6-dichloro-4-methylphenoxy)ethoxy]-phenyl}piperidine-1-carboxylate (1 eq.) from Example 1/Step 2 in DMF (0.1 M) was added cesium carbonate (2.5 eq.) and 2,2-dimethyloxirane (15 eq.). The reaction was stirred for 18 h at 50° C., then added more 2,2-dimethyloxirane (10 eq.). The reaction was heated to 80° C. and stirred for 4.5 h. After cooling to rt, the reaction was diluted with ether. The organic extract was washed with water, brine, dried over MgSO$_4$, and concentrated in vacuo. The crude product was purified by flash column chromatography (SiO$_2$, 45%→55% EtOAc in Hex) to afford the title compound as an oil.

Step 2: (3R,4S)-N-Cyclopropyl-4-{4-[2-(2,6-dichloro-4-methylphenoxy)ethoxy]-phenyl}-N-[3-(2-hydroxy-2-methylpropoxy)-5-(3-methoxypropyl)benzyl]piperidine-3-carboxamide To a solution of tert-butyl (3R,4S)-3-({cyclopropyl[3-(2-hydroxy-2-methyl-propoxy)-5-(3-methoxypropyl)benzyl]amino}carbonyl)-4-{4-[2-(2,6-dichloro-4-methylphenoxy)ethoxy]phenyl}piperidine-1-carboxylate in acetonitrile (0.02 M) at 0° C. was added iodotrimethylsilane (2 eq.) and stirred for 10 min at 0° C. The reaction was quenched with saturated aqueous NaHCO$_3$ solution and extracted with EtOAc. The combined organic extracts were washed with brine, dried over MgSO$_4$, and concentrated in vacuo. The residue was dissolved in THF (0.2 M) and added tetrabutylammonium fluoride (2 eq.), and the reaction was stirred for 1 h at rt. The reaction mixture was concentrated in vacuo. The crude product was purified by flash column chromatography (SiO$_2$, 7% [2 M NH$_3$ in MeOH] in DCM) to afford the title compound as a colorless oil. $^1$H NMR (acetone d-6): δ 7.30 (s, 2H), 7.20 (d, 2H), 6.85 (d, 2H), 6.65 (s, 1H), 6.55 (s, 1H), 6.38 (s, 1H), 4.30-4.45 (m, 6H), 3.50-3.80 (m, 4H), 3.00-3.48 (m, 8H), 2.70-2.90 (m, 2H), 2.55 (t, 2H), 2.30-2.40 (m, 4H), 1.70-1.85 (m, 4H), 1.30 (s, 6H), 0.4-0.9 (m, 4H). LRMS [M+H]=713.2

EXAMPLE 7

(3R,4S)-N-[3-{[1-(Cyanomethyl)cyclopropyl]methoxy}-5-(3-methoxypropyl)benzyl]-N-cyclopropyl-4-{4-[2-(2,6-dichloro-4-methylphenoxy)ethoxy]phenyl}piperidine-3-carboxamide

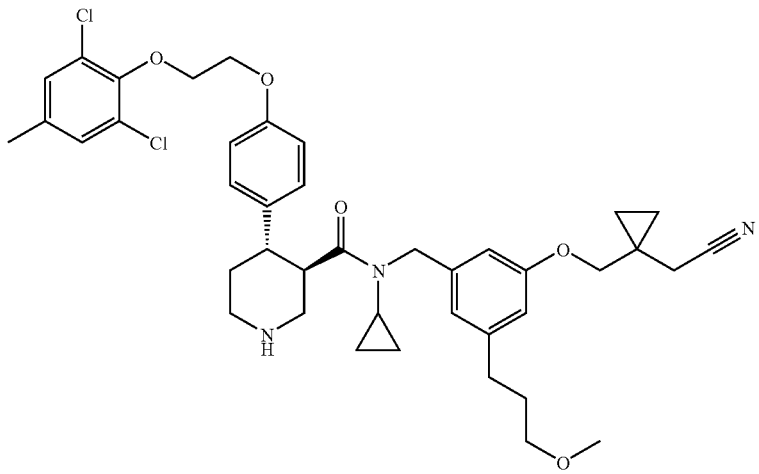

Step 1: [1-(Cyanomethyl)cyclopropyl]methyl methanesulfonate

To a solution of [1-(hydroxymethyl)cyclopropyl]acetonitrile (prepared according to the procedure described in WO2005/105749 Example 2/Step 4, incorporated by reference) (1 eq.) in DCM at −40° C. was added triethylamine (3 eq.) and then methanesulfonyl chloride (1.5 eq.). The reaction was warmed to −10° C. over 1 h, and it was diluted with DCM and quenched with saturated aqueous NaHCO$_3$. The aqueous phase was extracted with DCM. The combined organic extracts were dried over MgSO$_4$ and concentrated in vacuo. The crude product was purified by flash column chromatography (SiO$_2$, 0%→50% EtOAc in Hex) to afford the title compound as an oil.

Step 2: tert-Butyl (3R,4S)-3-{[[3-{[1-(cyanomethyl)cyclopropyl]methoxy}-5-(3-methoxypropyl)benzyl](cyclopropyl)amino]carbonyl}-4-{4-[2-(2,6-dichloro-4-methylphenoxy)ethoxy]phenyl}piperidine-1-carboxylate To a solution of tert-butyl (3R,4S)-3-({cyclopropyl[3-hydroxy-5-(3-methoxy-propyl)benzyl]-amino}carbonyl)-4-(4-{[2-(2,6-dichloro-4-methylphenoxy)ethoxy]-phenyl}piperidine-1-carboxylate (1 eq.) from Example 1/Step 2 in DMF (0.1 M) was added cesium carbonate (2 eq.) and [1-(cyanomethyl)cyclopropyl]methyl methanesulfonate (2 eq.) from the previous step. The reaction was heated to 80° C. and stirred for 18 h. After cooling to rt, the reaction was diluted with ether. The organic extract was washed with water, brine, dried over MgSO$_4$, and concentrated in vacuo. The crude product was purified by flash column chromatography (SiO$_2$, 0%→50% EtOAc in Hex) to afford the title compound as an oil.

Step 3: (3R,4S)-N-[3-{[1-(Cyanomethyl)cyclopropyl]methoxy}-5-(3-methoxypropyl)-benzyl]-N-cyclopropyl-4-{4-[2-(2,6-dichloro-4-methylphenoxy)ethoxy]phenyl}-piperidine-3-carboxamide Prepared according to the procedure described in Example 1/Step 4 but using instead tert-butyl (3R,4S)-3-{[[3-{[1-(cyanomethyl)cyclopropyl]methoxy}-5-(3-methoxypropyl)benzyl](cyclopropyl)amino]carbonyl}-4-{4-[2-(2,6-dichloro-4-methylphenoxy)ethoxy]phenyl}piperidine-1-carboxylate from the previous step as the starting material. The title compound was a colorless oil. $^1$H NMR (acetone d-6): δ 7.30 (s, 2H), 7.20 (d, 2H), 6.45 (d, 2H), 6.65 (s, 1H), 6.55 (s, 1H), 6.40 (s, 1H), 4.30-4.45 (m, 6H), 3.9 (s, 2H), 3.55 (dt, 1H), 3.00-3.45 (m, 8H), 2.70-2.90 (m, 4H), 2.55 (t, 2H), 2.30-2.40 (m, 4H), 1.70-1.85 (m, 4H), 0.4-0.9 (m, 8H). LRMS [M+H]=734.3

EXAMPLE 8

(3R,4S)-N-Cyclopropyl-4-{4-[2-(2,6-dichloro-4-methylphenoxy)ethoxy]phenyl}-N-([3-{[(1R,2R)-2-(hydroxymethyl)cyclopropyl]methoxy}-5-(3-methoxypropyl)benzyl]-piperidine-3-carboxamide

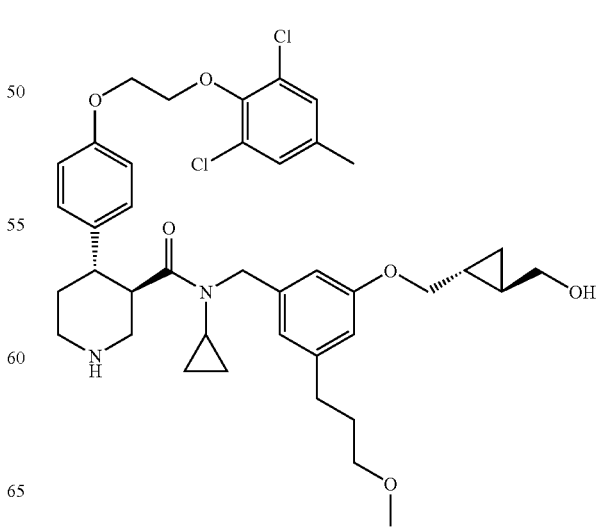

Step 1: Ethyl (1R,2R)-2-(hydroxylmethyl)cyclopropanecarboxylate

To a solution of ethyl 2-formyl-1-cyclopropanecarboxylate (1.5 eq.) in methanol (0.7 M) at 0° C. was added sodium borohydride (1.5 eq.) in portions over 30 min. The mixture was allowed to stir at rt for 1.5 h and then cooled in an ice bath. Saturated aqueous NH$_4$Cl solution was added dropwise, and the mixture was stirred for 1.5 h. Water was added, and the aqueous layer was extracted with EtOAc. The combined organic extracts were washed with brine, dried over MgSO$_4$, and concentrated to afford a racemic mixture of the title compound as a clear oil. Racemic trans 2-(hydroxymethyl)cyclopropanecarboxylate was purified by a Chiral Pak AD preparative column (10% EtOH/Hex) to afford two enantiomers. Ethyl (1R,2R)-2-(hydroxymethyl)cyclopropanecarboxylate was eluted as the faster enantiomer (retention time=12.94 min).

Step 2: tert-Butyl (3R,4S)-3-({cyclopropyl[3-{[(1R,2R)-2-(ethoxycarbonyl)cyclo-propyl]methoxy}-5-(3-methoxypropyl)benzyl]amino}carbonyl)-4-{4-[2-(2,6-di-chloro-4-methylphenoxy)ethoxy]phenyl}piperidine-1-carboxylate To a solution of tert-butyl(3R,4S)-3-({cyclopropyl[3-hydroxy-5-(3-methoxy-propyl)benzyl]amino}carbonyl)-4-{4-[2-(2,6-dichloro-4-methylphenoxy)ethoxy]-phenyl}piperidine-1-carboxylate (1 eq.) from Example 1/Step 2 in toluene (0.1 M) was added 1,1'-(azodicarbonyl)dipiperidine (1.2 eq.), ethyl (1R,2R)-2-(hydroxyl-methyl)cyclopropanecarboxylate (2 eq.) from the previous step, and tri-n-butylphosphine (1.2 eq.). The reaction was heated to 80° C. and stirred for 18 h. While hot, the reaction was diluted with EtOAc/water. The aqueous layer was extracted with EtOAc. The combined organic extracts were washed with brine, dried over MgSO$_4$, and concentrated in vacuo. The crude product was purified by flash column chromatography (SiO$_2$, 40% EtOAc in Hex) to afford the title compound as an oil.

Step 3: tert-Butyl (3R,4S)-3-({cyclopropyl[3-{[(1R,2R)-2-(hydroxymethyl)cyclo-propyl]methoxy}-5-(3-methoxypropyl)benzyl]amino}carbonyl)-4-{4-[2-(2,6-di-chloro-4-methylphenoxy)ethoxy]phenyl}piperidine-1-carboxylate To a solution of tert-butyl (3R,4S)-3-({cyclopropyl[3-{[(1R,2R)-2-(ethoxycarbonyl)cyclopropyl]methoxy}-5-(3-methoxypropyl)benzyl]amino}-carbonyl)-4-{4-[2-(2,6-dichloro-4-methylphenoxy)ethoxy]phenyl}piperidine-1-carboxylate (1 eq.) from the previous step in THF at −78° C. was added diisobutylaluminum hydride (3 eq.). The reaction was stirred at −78° C. for 1 h and then warmed to rt. EtOAc and aqueous Rochelle's salt solution were added and stirred until the two phases separated. The aqueous layer was extracted with EtOAc. The combined organic extracts were washed with brine, dried over MgSO$_4$, and concentrated in vacuo. The crude product was purified by flash column chromatography (SiO$_2$, 60% EtOAc in Hex) to afford the title compound as an oil.

Step 4: (3R,4S)-N-Cyclopropyl-4-{4-[2-(2,6-dichloro-4-methylphenoxy)ethoxy]-phenyl}-N-[3-{[(1R,2R)-2-(hydroxymethyl)cyclopropyl]methoxy}-5-(3-methoxy-propyl)benzyl]-piperidine-3-carboxamide Prepared according to the procedure described in Example 1/Step 4 but using instead tert-butyl (3R,4S)-3-({cyclopropyl [3-{[(1R,2R)-2-(hydroxymethyl)cyclo-propyl]methoxy}-5-(3-methoxypropyl)benzyl]amino}carbonyl)-4-{4-[2-(2,6-di-chloro-4-methylphenoxy)ethoxy]phenyl}piperidine-1-carboxylate from the previous step as the starting material. The title compound was a colorless oil. $^1$H NMR (acetone d-6): δ 7.24 (s, 2H), 7.16 (d, 2H), 6.81 (d, 2H), 6.56 (s, 1H), 6.45 (s, 1H), 6.34 (s, 1H), 4.34 (m, 6H), 3.86 (m, 1H), 3.72 (m, 1H), 3.54 (m, 1H), 3.44 (d, 2H), 3.3 (m, 3H), 3.24 (s, 3H), 3.2 (m, 1H), 3.11 (m, 1H), 3.06 (m, 1H), 2.73 (m, 2H), 2.5 (t, 2H), 2.3 (s, 3H), 2.29 (m, 1H), 1.75 (m, 4H), 1.15 (m, 1H), 1.05 (m, 1H), 0.75 (m, 3H), 0.52 (t, 2H), 0.42 (m, 1H). LRMS [M+H] =725.2

EXAMPLE 9

(3R,4S)-N-[3-Acetyl-5-(3-methoxypropyl)benzyl]-N-cyclopropyl-4-{4-[2-(2,6-di-chloro-4-methylphenoxy)ethoxy]phenyl}piperidine-3-carboxamide

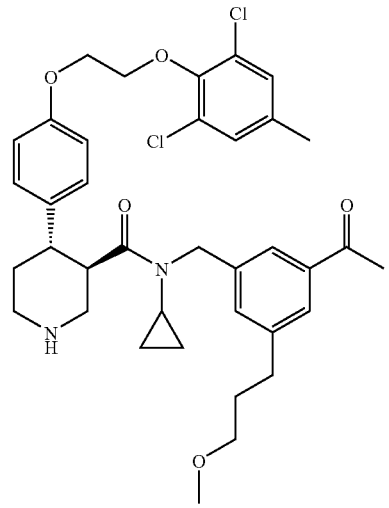

Step 1: tert-Butyl (3R,4S)-3-{[cyclopropyl(3-(3-methoxypropyl)-5-{[(trifluoro-methyl)sulfonyl]oxy}benzyl)amino]carbonyl}-4-{4-[2-(2,6-dichloro-4-methylphen-oxy)ethoxy]phenyl}piperidine-1-carboxylate To a solution of tert-butyl (3R,4S)-3-({cyclopropyl[3-hydroxy-5-(3-methoxy-propyl)benzyl]-amino}carbonyl)-4-{4-[2-(2,6-dichloro-4-methylphenoxy)ethoxy]-phenyl}piperidine-1-carboxylate (1 eq.) from Example 1/Step 2 in DCM (0.1 M) at 0° C. was added triethylamine (2.5 eq.) and trifluoromethanesulfonic anhydride (1.2 eq.). The reaction was stirred at 0° C. for 1 h and then quenched with saturated aqueous NaHCO$_3$ solution. The aqueous layer was extracted with EtOAc. The combined organic extracts were washed with brine, dried over Na$_2$SO$_4$, and concentrated in vacuo. The crude product was purified by flash column chromatography (SiO$_2$, 10%→30% EtOAc in DCM) to afford the title compound as a colorless oil.

Step 2: tert-Butyl (3R,4S)-3-{[[3-acetyl-5-(3-methoxypropyl)benzyl](cyclopropyl)-amino]carbonyl}-4-{4-[2-(2,6-dichloro-4-methylphenoxy)ethoxy]phenyl}piperidine-1-carboxylate To a solution of tert-butyl (3R,4S)-3-{[cyclopropyl(3-(3-methoxypropyl)-5-{[(trifluoromethyl)sulfonyl]oxy}benzyl)amino]carbonyl}-4-{4-[2-(2,6-dichloro-4-methylphen-oxy)ethoxy]phenyl}piperidine-1-carboxylate (1 eq.) from the previous step in dioxane (0.07 M) was added tributyl(1- ethoxyvinyl)stannane (1.2 eq.), palladium tetrakis(triphenylphosphine) (5 mol %), and LiCl (3 eq.). The reaction was heated to reflux and stirred for 18 h. After cooling to rt, the reaction was quenched with saturated aqueous NaHCO₃ solution. The aqueous layer was extracted with EtOAc. The combined organic extracts were washed with brine, dried over Na₂SO₄, and concentrated in vacuo. The residue was dissolved in THF (0.07 M) and added 2 M aqueous HCl (5 eq.), and the reaction was stirred at rt for 30 min. The reaction was quenched with saturated aqueous NaHCO₃ solution. The aqueous layer was extracted with EtOAc. The combined organic extracts were washed with brine, dried over Na₂SO₄, and concentrated in vacuo. The crude product was purified by flash column chromatography (SiO₂, 50%→360% EtOAc in Hex) to afford the title compound as an oil.

Step 3: (3R,4S)-N-[3-Acetyl-5-(3-methoxypropyl) benzyl]-N-cyclopropyl-4-{4-[2-(2,6-dichloro-4-methylphenoxy)ethoxy]phenyl}piperidine-3-carboxamide Prepared according to the procedure described in Example 1/Step 4 but using instead tert-butyl (3R,4S)-3-{[[3-acetyl-5-(3-methoxypropyl)benzyl](cyclopropyl)-amino]carbonyl}-4-{4-[2-(2,6-dichloro-4-methylphenoxy)ethoxy] phenyl}piperidine-1-carboxylate from the previous step as the starting material. The title compound was a colorless oil. ¹H NMR (CDCl₃): δ 7.62 (s, 1 H), 7.49 (s, 1 H), 7.16-7.10 (m, 4 H), 7.01 (s, 1 H), 6.74 (d, 2 H), 4.48 (d, 1 H), 4.38-4.25 (m, 5 H), 3.39-3.22 (m, 7 H), 3.18-2.85 (m, 3 H), 2.68 (t, 2 H), 2.58 (s, 3 H), 2.31, (s, 3 H), 2.20-2.15 (m, 1 H), 1.96-1.81 (m, 4 H), 1.65-1.50 (m, 1 H), 0.99-0.89 (m, 1 H), 0.-0.69 (m, 2 H), 0.53-0.46 (m, 1 H). LRMS [M+H]=667.2

EXAMPLE 10

(3R,4S)-N-Cyclopropyl-4-{4-[2-(2,6-dichloro-4-methylphenoxy)ethoxy]phenyl}-N-[3-(2-methoxyethoxy)-5-(2-methoxyethyl)benzyl]piperidine-3-carboxamide

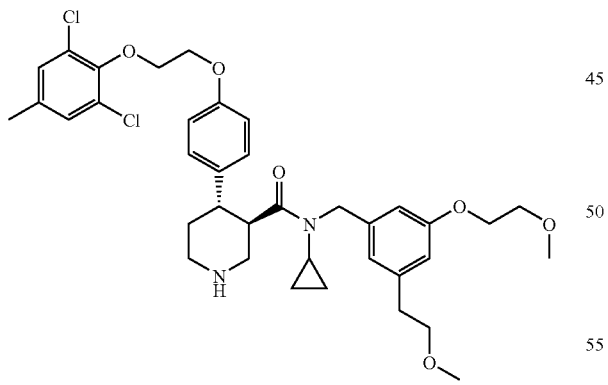

Prepared according to the procedure described in Example 1 but using instead N-[3-(2-methoxyethoxy)-5-(2-methoxyethyl)benzyl]cyclopropanamine (amine 2) as the starting material. The title compound was a colorless oil. ¹H NMR (acetone d-6): δ 7.29 (s, 2H), 7.20 (d, 2H), 6.84 (d, 2H), 6.66 (s, 1H), 6.50 (s, 1H), 6.40 (s, 1H), 4.30-4.45 (m, 5H), 4.25 (d, 1H), 4.04 (t, 2H), 3.70 (t, 2H), 3.48-3.60 (m, 3H), 3.38 (s, 3H), 3.28 (s, 3H), 3.00-3.25 (m, 3H), 2.68-2.85 (m, 4H), 2.30-2.38 (m, 4H), 1.68-1.80 (m, 2H), 0.4-0.9 (m, 4H). LRMS [M+H]=685.3

EXAMPLE 11

(3R,4S)-N-[3,5-Bis(3-methoxypropyl)benzyl]-N-cyclopropyl-4-{4-[2-(2,6-dichloro-4-methylphenoxy)ethoxy]phenyl}piperidine-3-carboxamide

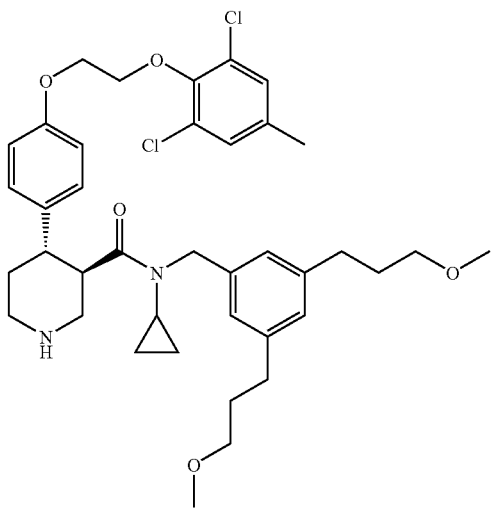

Prepared according to the procedure described in Example 1 but using instead N-[3,5-bis(3-methoxypropyl)benzyl]cyclopropanamine (amine 3) as the starting material. The title compound was a colorless oil. ¹H NMR (acetone d-6): δ 7.29 (s, 2H), 7.22 (d, 2H), 6.87 (s, 1H), 6.86 (d, 2H), 6.63 (s, 2H), 4.5 (d, 1H), 4.39 (m, 4H), 4.25 (d, 1H), 3.58 (m, 1H), 3.33 (t, 4H), 3.28 (s, 6H), 3.23 (m, 1H), 3.11 (m, 2H), 2.76 (m, 2H), 2.56 (t, 4H), 2.37 (m, 1H), 2.35 (s, 3H), 1.79 (m, 6H), 0.75 (m, 3H), 0.50 (m, 1H). LRMS [M+H]=697.5

EXAMPLE 12

(3R,4S)-N-[3,5-Bis(2-methoxyethoxy)benzyl]-N-cyclopropyl-4-{4-[2-(2,6-dichloro-4-methylphenoxy)ethoxy]phenyl}piperidine-3-carboxamide

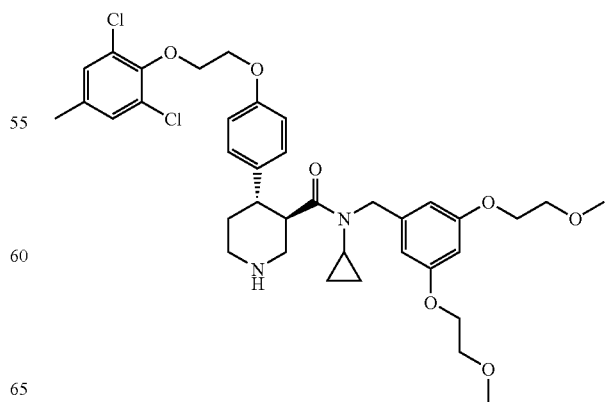

Prepared according to the procedure described in Example 1 but using instead N-[3,5-bis(2-methoxyethoxy)benzyl]cyclopropanamine (amine 4) as the starting material. The title compound was a colorless oil. $^1$H NMR (acetone d-6): δ 7.28 (s, 2H), 7.18 (d. 2H), 6.82 (d, 2H), 6.33 (s, 1H), 6.21-6.26 (m, 2H), 4.30-4.40 (m, 6H), 4.02 (t, 4H), 3.70 (t, 4H), 3.51 (dt, 1H), 3.35 (s, 6H), 3.00-3.24 (m, 3H), 2.65-2.85 (m, 2H), 2.30-2.35 (m, 4H), 1.65-1.80 (m, 2H), 0.4-0.9 (m, 4H). LRMS [M+H]=701.3

Inhibition of Human Recombinant Renin

The enzymatic in vitro assay was performed in 384-well polypropylene plates (Nunc). The assay buffer consisted of PBS (Gibco BRL) including 1 mM EDTA and 0.1% BSA. The reaction mixture were composed of 47.5 µL per well of an enzyme mix and 2.5 µL of renin inhibitors in DMSO. The enzyme mix was premixed at 4° C. and consists of the following components:

human recombinant renin (40 pM)
synthetic human angiotensin(1-14) (0.5 µM)
hydroxyquinoline sulfate (1 mM)

The mixtures were then incubated at 37° C. for 3 h. The enzyme reaction was stopped by placing the reaction plate on wet ice.

To determine the enzymatic activity and its inhibition, the accumulated Ang I was detected by an enzyme immunoassay (EIA) in 384-well plates (Nunc). 5 µL of the reaction mixture or standards were transferred to immuno plates which were previously coated with a covalent complex of Ang I and bovine serum albumin (Ang I-BSA). 75 µL of Ang I-antibodies in assay buffer above including 0.01% Tween 20 were added and the plates were incubated at 4° C. overnight.

An alternative protocol could be used by stopping the enzymatic reaction with 0.02N final concentration of HCl. 5 µL of the reaction mixture or standards were transferred to immuno plates and 75 µL of Ang I-antibodies in assay buffer above including 0.01% Tween 20 were added and the plates were incubate at RT for 4 h.

The plates were washed 3 times with PBS including 0.01% Tween 20, and then incubated for 2 h at RT with an anti rabbit-peroxidase coupled antibody (WA 934, Amersham). After washing the plates 3 times, the peroxidase substrate ABTS ((2,2'-Azino-bis(3-ethylbenzthiazoline-6-sulfonic Acid) 2NH$_3$) was added and the plates incubated for 60 min at RT. The plate was evaluated in a microplate reader at 405 nm. The percentage of inhibition was calculated for each concentration point and the concentration of renin inhibition was determined that inhibited the enzyme activity by 50% ($IC_{50}$). The $IC_{50}$-values of all compounds tested were below 1 □M.

Inhibition of Renin in Human Plasma

The enzymatic in vitro assay was performed in 384-well polypropylene plates (Nunc). The assay buffer consisted of PBS (Gibco BRL) including 1 mM EDTA and 0.1% BSA. The reaction mixture was composed of 80 µL per well of human plasma, enzyme, Ang I-antibodies mix and 5 µL of renin inhibitors in DMSO. The human plasma mix was premixed at 4° C. and consists of human plasma from 10 normal donors
human recombinant renin (3 pM)
Ang I-antibodies.

The mixtures were then incubated at 37° C. for 2 h.

To determine the enzymatic activity and its inhibition, the accumulated Ang I was detected by an enzyme immunoassay (EIA) in 384-well plates (Nunc). 10 µL of the reaction mixture or standards were transferred to immuno plates which were previously coated with a covalent complex of Ang I and bovine serum albumin (Ang I-BSA). 70 µL assay buffer were added and the plates were incubated at 4° C. overnight. The plates were washed 3 times with PBS including 0.01% Tween 20, and then incubated for 2 h at RT with an anti rabbit-peroxidase coupled antibody (WA 934, Amersham). After washing the plates 3 times, the peroxidase substrate ABTS ((2,2'-Azino-bis(3-ethylbenzthiazoline-6-sulfonic Acid) 2NH$_3$) was added and the plates incubated for 60 min at RT. The plate was evaluated in a microplate reader at 405 nm. The percentage of inhibition was calculated of each concentration point and the concentration of renin inhibition was determined that inhibited the enzyme activity by 50% ($IC_{50}$). The $IC_{50}$-values of all compounds tested were below 10 □M.

In vivo animal model—Female double transgenic rats were purchased from RCC Ltd, Füllingsdorf, Switzerland. All animals were maintained under identical conditions and had free access to normal pelleted rat chow and water. Rats were initially treated with enalapril (1 mg/kg/day) during 2 months. After approximately two weeks following cessation of enalapril treatment the double transgenic rats become hypertensive and reach mean arterial blood pressures in the range of 160-170 mmHg.

Transmitter implantation—The rats were anaesthetized with a mixture of 90 mg/kg Ketamin-HCl (Ketavet, Parke-Davis, Berlin FRG) and 10 mg/kg xylazin (Rompun, Bayer, Leverkusen, FRG) i.p. The pressure transmitter was implanted under aseptic conditions into the peritoneal cavity with the sensing catheter placed in the descending aorta below the renal arteries pointing upstream. The transmitter was sutured to the abdominal musculature and the skin closed.

Telemetry-System—Telemetry units were obtained from Data Sciences (St. Paul, Minn.). The implanted sensor consisted of a fluid-filled catheter (0.7 mm diameter, 8 cm long; model TA11PA-C40) connected to a highly stable low-conductance strain-gauge pressure transducer, which measured the absolute arterial pressure relative to a vacuum, and a radio-frequency transmitter. The tip of the catheter was filled with a viscous gel that prevents blood reflux and was coated with an antithrombogenic film to inhibit thrombus formation. The implants (length=2.5 cm, diameter=1.2 cm) weighted 9 g and have a typical battery life of 6 months. A receiver platform (RPC-1, Data Sciences) connected the radio signal to digitized input that was sent to a dedicated personal computer (Compaq, deskpro). Arterial pressures were calibrated by using an input from an ambient-pressure reference (APR-1, Data Sciences). Systolic, mean and diastolic blood pressure was expressed in millimeter of mercury (mmHg).

Hemodynamic measurements—Double transgenic rats with implanted pressure transmitters were dosed by oral gavage with vehicle or 10 mg/kg of the test substance (n=6 per group) and the mean arterial blood pressure was continuously monitored. The effect of the test substance is expressed as maximal decrease of mean arterial pressure (MAP) in the treated group versus the control group.

Biological Activities
| Compound | Structure | Renin buffer (nM) | Renin plasma (nM) |
|---|---|---|---|
| Example 1 | 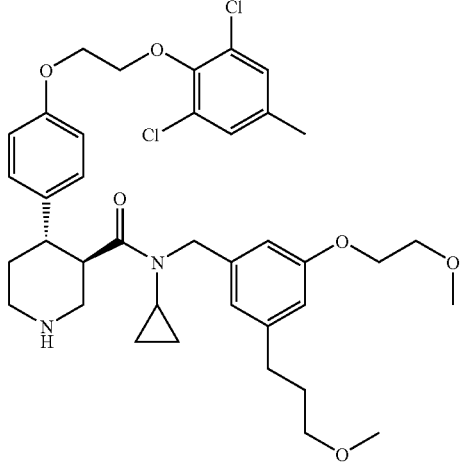 | 0.022 | 4.4 |
| Example 2 | 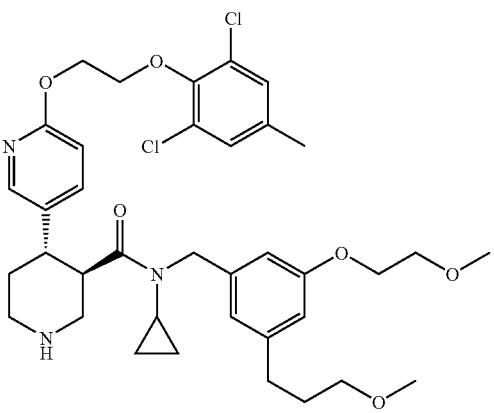 | 0.022 | 6.0 |
| Example 4 | 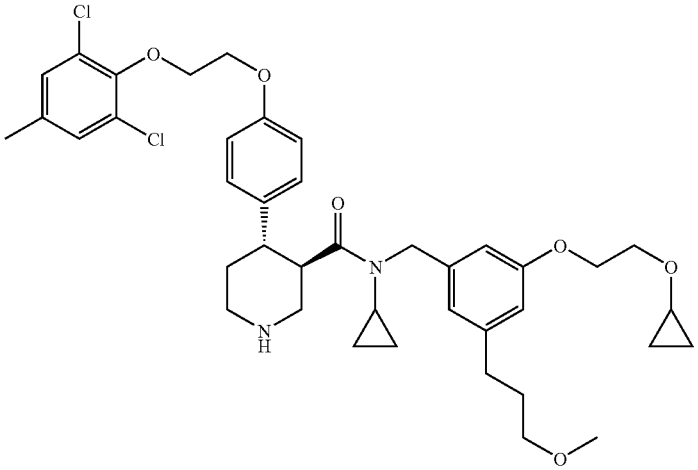 | 0.044 | 4.0 |

-continued

| Compound | Structure | Renin buffer (nM) | Renin plasma (nM) |
|---|---|---|---|
| Example 8 | 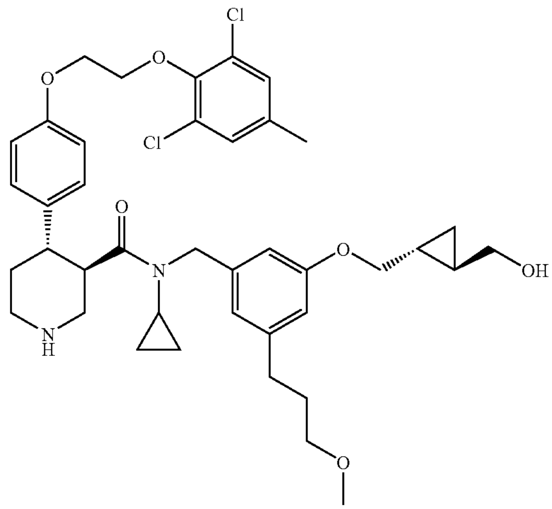 | 0.036 | 2.6 |
| Example 11 | 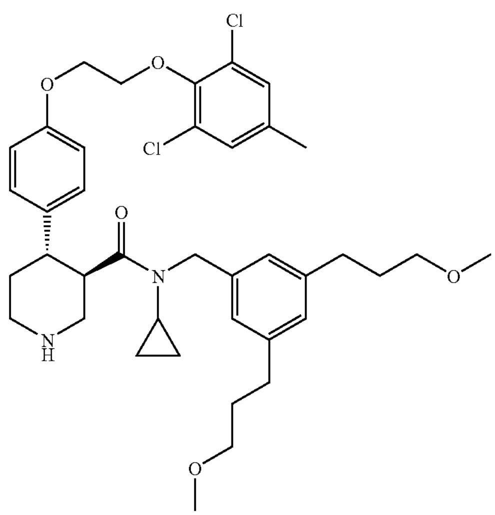 | 0.038 | 8.7 |

What is claimed is:

1. A compound of formula I,

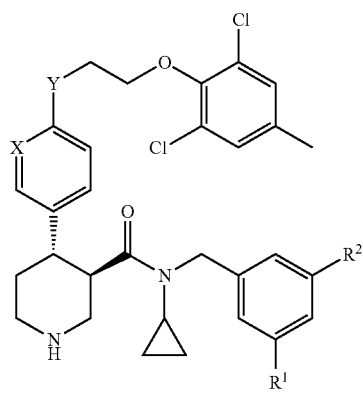

or a pharmaceutically acceptable salt thereof, or an optical isomer thereof, wherein X is N or CH;

Y is O, $CH_2$, or a bond;

$R^1$ is
—$(CH_2)_{1-3}OR^4$, or
—$O(CH_2)_{1-2}OR^4$;

$R^2$ is selected from the group consisting of
—$(CH_2)_{1-5}OR^4$,
—$O(CH_2)_{2-4}OR^4$,
—$C(O)R^4$,
—$OR^4$,
—$O(CH_2)_{2-4}O$—($C_3$-$C_8$cycloalkyl), wherein cycloalkyl is unsubstituted or substituted with $C_1$-$C_4$alkyl or $C_1$-$C_4$alkanol,
—$O(CH_2)_{2-4}NR^4R^5$,

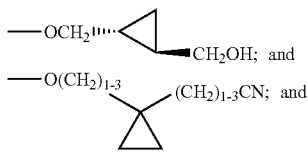

$R^4$ and $R^5$ are independently $C_1$-$C_6$alkyl unsubstituted or substituted with —OH or $CF_3$.

2. A compound of claim 1, or a pharmaceutically acceptable salt thereof, wherein $R^1$ is —$(CH_2)_3OCH_3$, —$(CH_2)_2OCH_3$ or —$O(CH_2)_2OCH_3$.

3. A compound of claim 1, or a pharmaceutically acceptable salt thereof, wherein Y is O.

4. A compound of claim 1, or a pharmaceutically acceptable salt thereof, wherein
$R^2$ is selected from the group consisting of
—$(CH_2)_3OR^4$,
—O—$(CH_2)_2OR^4$,
—$C(O)R^4$,
—$OR^4$,
—$O(CH_2)_2O$—$(C_3$-$C_8$cycloalkyl), wherein cycloalkyl is unsubstituted or substituted with $C_1$-$C_4$alkyl or $C_1$-$C_4$alkanol,
—$O(CH_2)_2NR^4R^5$, and

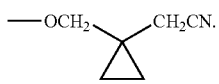

5. A compound of claim 1, or a pharmaceutically acceptable salt thereof, wherein
$R^2$ is selected from the group consisting of
—$(CH_2)_3OCH_3$,
—$O(CH_2)_2OCH_3$,
—$C(O)CH_3$,
—$OCH_2C(CH_3)_2OH$,
—$O(CH_2)_2OCH_2CF_3$,
—$O(CH_2)_2OCH_3$,
—$O(CH_2)_2N(CH_3)_2$,

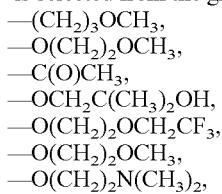

6. A compound of claim 1, or a pharmaceutically acceptable salt thereof, wherein
$R^4$ and $R^5$ are independently selected from the group consisting of —$CH_3$, —$CH_2CF_3$, and —$(CH_2)C(CH_3)_2OH$.

7. A compound of claim 1, or a pharmaceutically acceptable salt thereof, selected from the group consisting of:
(3R,4S)-N-Cyclopropyl-4-{4-[2-(2,6-dichloro-4-methylphenoxy)ethoxy]phenyl}-N-[3-(2-methoxyethoxy)-5-(3-methoxypropyl)benzyl]piperidine-3-carboxamide,
(3R,4S)-N-Cyclopropyl-4-{6-2-[2,6-dichloro-4-methylphenoxy)ethoxy]pyridin-3-yl}-N-[3-(2-methoxyethoxy)-5-(3-methoxypropyl)benzyl]piperidine-3-carboxamide,
(3R,4S)-N-Cyclopropyl-4-{4-[2-(2,6-dichloro-4-methylphenoxy)ethoxy]phenyl}-N-[3-[2-(dimethylamino)ethoxy]-5-(3 -methoxypropyl)benzyl]piperidine-3-carboxamide,
(3R,4S)-N-Cyclopropyl-N-[3-[2-(cyclopropyloxy)ethoxy]-5-(3 -methoxypropyl)-benzyl]-4-{4-[2-(2,6-dichloro-4-methylphenoxy)ethoxy]phenyl}piperidine-3-carboxamide,
(3R,4S)-N-Cyclopropyl-4-{4-[2-(2,6-dichloro-4-methylphenoxy)ethoxy]phenyl}-N-{3-3-methoxypropyl)-5-[2-(2,2,2-trifluoroethoxy)ethoxy]benzyl}piperidine-3-carboxamide,
(3R,4S)-N-Cyclopropyl-4-{4-[2-(2,6-dichloro-4-methylphenoxy)ethoxy]phenyl}-N-[3-(2-hydroxy-2-methylpropoxy)-5-(3-methoxypropyl)benzyl]piperidine-3-carboxamide,
(3R,4S)-N-[3-{[1-(Cyanomethyl)cyclopropyl]methoxy}-5 -(3-methoxypropyl)benzyl]-N-cyclopropyl-4-{4-[2-(2,6-dichloro-4-methylphenoxy)ethoxy]phenyl}piperidine-3-carboxamide,
(3R,4S)-N-Cyclopropyl-4-{4-[2-(2,6-dichloro-4-methylphenoxy)ethoxy]phenyl}-N-[3-{[(1R,2R)-2-(hydroxymethyl)cyclopropyl]methoxy}-5-(3-methoxypropyl)benzyl]-piperidine-3 -carboxamide,
(3R,4S)-N-[3-Acetyl-5-(3-methoxypropyl)benzyl]-N-cyclopropyl-4-{4-[2-(2,6-di-chloro-4-methylphenoxy)ethoxy]phenyl}piperidine-3-carboxamide,
(3R,4S)-N-Cyclopropyl-4-{4-[2-(2,6-dichloro-4-methylphenoxy)ethoxy]phenyl}-N-[3-(2-methoxyethoxy)-5-(2-methoxyethyl)benzyl]piperidine-3-carboxamide,
(3R,4S)-N-[3 ,5-Bis(3-methoxypropyl)benzyl]-N-cyclopropyl-4-{4-[2-(2,6-dichloro-4-methylphenoxy)ethoxy]phenyl}piperidine-3-carboxamide, and
(3R,4S)-N-[3,5-Bis(2-methoxyethoxy)benzyl]-N-cyclopropyl-4- {4-[2-(2,6-dichloro-4-methylphenoxy)ethoxy]phenyl}piperidine-3-carboxamide.

8. A pharmaceutical composition comprising an effective amount of a compound according to claim 1, or a pharmaceutically acceptable salt thereof, and a pharmaceutically acceptable carrier.

9. A method for the treatment of hypertension, comprising the administration to a patient of a pharmaceutically active amount of a compound according to claim 1.

* * * * *